US010744192B2

(12) United States Patent
Fontaine et al.

(10) Patent No.: US 10,744,192 B2
(45) Date of Patent: Aug. 18, 2020

(54) VACCINE

(71) Applicant: Moredun Research Institute, Penicuik, Midlothian (GB)

(72) Inventors: Michael Christopher Fontaine, Edinburgh (GB); David George Emslie Smith, Edinburgh (GB); Julie Lydia Fitzpatrick, Edinburgh (GB); William Donachie, Edinburgh (GB); Anita Dorota Jaglarz, Edinburgh (GB)

(73) Assignee: Moredun Research Institute, Penicuik (GB)

( * ) Notice: Subject to any disclaimer, the term of this patent is extended or adjusted under 35 U.S.C. 154(b) by 18 days.

(21) Appl. No.: 15/074,689

(22) Filed: Mar. 18, 2016

(65) Prior Publication Data
US 2016/0193318 A1 Jul. 7, 2016

Related U.S. Application Data

(63) Continuation of application No. PCT/US2014/056591, filed on Sep. 19, 2014.

(60) Provisional application No. 61/879,959, filed on Sep. 19, 2013.

(51) Int. Cl.
*A61K 39/09* (2006.01)
*A61K 39/00* (2006.01)
*A61K 39/012* (2006.01)
*A61K 39/108* (2006.01)
*A61K 39/05* (2006.01)
*A61K 39/08* (2006.01)
*A61K 39/118* (2006.01)
*A61K 39/39* (2006.01)
*A61K 39/002* (2006.01)
*A61K 39/085* (2006.01)
*A61K 39/12* (2006.01)
*G01N 33/569* (2006.01)

(52) U.S. Cl.
CPC ........ *A61K 39/092* (2013.01); *A61K 39/0002* (2013.01); *A61K 39/002* (2013.01); *A61K 39/0003* (2013.01); *A61K 39/0005* (2013.01); *A61K 39/012* (2013.01); *A61K 39/0258* (2013.01); *A61K 39/05* (2013.01); *A61K 39/08* (2013.01); *A61K 39/085* (2013.01); *A61K 39/118* (2013.01); *A61K 39/12* (2013.01); *A61K 39/39* (2013.01); *G01N 33/56944* (2013.01); *A61K 2039/552* (2013.01); *A61K 2039/55561* (2013.01); *A61K 2039/55566* (2013.01); *A61K 2039/55572* (2013.01); *A61K 2039/55577* (2013.01); *A61K 2039/55583* (2013.01); *G01N 2333/315* (2013.01); *G01N 2469/10* (2013.01); *Y02A 50/474* (2018.01)

(58) Field of Classification Search
None
See application file for complete search history.

(56) References Cited

U.S. PATENT DOCUMENTS

| 7,939,087 | B2* | 5/2011 | Telford | C07K 14/315 424/184.1 |
|---|---|---|---|---|
| 7,955,604 | B2* | 6/2011 | Telford | C07K 14/315 424/184.1 |
| 9,738,693 | B2* | 8/2017 | Telford | C07K 14/315 |
| 9,840,538 | B2* | 12/2017 | Telford | C07K 14/315 |
| 2013/0039947 | A1* | 2/2013 | Malley | A61K 39/092 424/244.1 |
| 2015/0111760 | A1* | 4/2015 | Bergeron | C12Q 1/14 506/2 |
| 2015/0140034 | A1* | 5/2015 | Dominowski | A61K 39/002 424/203.1 |
| 2016/0015047 | A1* | 1/2016 | Gawande | A23B 4/20 424/450 |
| 2016/0193318 | A1* | 7/2016 | Fontaine | A61K 39/002 424/244.1 |
| 2017/0028050 | A1* | 2/2017 | Malley | A61K 39/092 |
| 2018/0015061 | A1* | 1/2018 | Gawande | A61K 31/198 |

FOREIGN PATENT DOCUMENTS

| EP | 2023143 A1 | 2/2009 | |
|---|---|---|---|
| WO | WO 2010/041056 A1 | 4/2010 | |
| WO | WO-2011112906 A2 * | 9/2011 | ........... A61K 39/092 |
| WO | WO-2015042369 A2 * | 3/2015 | ........... A61K 39/002 |
| WO | WO-2015042423 A2 * | 3/2015 | ........... A61K 39/002 |
| WO | WO-2015042449 A2 * | 3/2015 | ........... A61K 39/002 |

OTHER PUBLICATIONS

Khazandi et al, Journal of Dairy Research, 2015, 82:470-477. first published online Jul. 20, 2015 (Year: 2015).*
Perrig et al, Microbial Pathogenesis, 2017, 105:273-279. available online Mar. 1, 2017 (Year: 2017).*
Collado et al, Vaccine, 2016, 34:3848-3854. available online Jun. 6, 2016 (Year: 2016).*
International Search Report and Written Opinion, PCT/US2014/056591, dated Jun. 27, 2016.
Ward PN et al. Evidence for niche adaptation in the genome of the bovine pathogen *Streptococcus uberis*. BMC Genomics. Jan. 28, 2009; 10(1): 54.
Prado ME et al. Vaccination of dairy cows with recombinant *Streptococcus uberis* adhesion molecule induces antibodies that reduce adherence to and internalization of *S. uberis* into bovine mammary epithelial cells. Veterinary Immunology and Immunopathology. Jun. 15, 2011; 141(3-4): 201-208.

(Continued)

*Primary Examiner* — Nita M. Minnifield
(74) *Attorney, Agent, or Firm* — Myers Bigel, P.A.

(57) ABSTRACT

The invention is based upon the identification of a number of antigens derived from a species of the genus *Streptococcus*, which are cross reactive and which may serve as the basis of useful compositions and tests and procedures capable of identifying and/or detecting *Streptococcus* sp in samples.

4 Claims, No Drawings

Specification includes a Sequence Listing.

(56) References Cited

OTHER PUBLICATIONS

Denis M et al. Vaccines against bovine mastitis in the New Zealand context: What is the best way forward? New Zealand Veterinary Journal. Jun. 1, 2009; 57(3): 132-140.

* cited by examiner

# VACCINE

RELATED APPLICATIONS

This application is a continuation of PCT Application No. PCT/US2014/056591, filed on Sep. 19, 2014, which claims priority from U.S. Provisional Application No. 61/879,959, filed on Sep. 19, 2013, the contents of each of which are incorporated herein by reference in their entireties. The above-referenced PCT International Application was published as International Publication No. WO 2015/042423 A2 on Mar. 26, 2015.

STATEMENT REGARDING ELECTRONIC FILING OF A SEQUENCE LISTING

A Sequence Listing in ASCII text format, submitted under 37 C.F.R. § 1.821, entitled 9013-147CT_ST25.txt, 22,655 bytes in size, generated on Mar. 16, 2016 and filed via EFS-Web, is provided in lieu of a paper copy. This Sequence Listing is hereby incorporated by reference into the specification for its disclosures.

FIELD OF THE INVENTION

The present invention provides streptococcal antigens capable of raising host immune responses and for use as vaccines to protect against and/or reduce instances of *Streptococcus* infections. Furthermore, the invention provides streptococcal antigens which may find application in the diagnosis of Streptococcal infections and/or diseases and/or the detection or identification of specific streptococcal species.

BACKGROUND OF THE INVENTION

*Streptococcus uberis* is an important mastitis-causing pathogen, responsible for a large proportion of both clinical and sub-clinical cases of mastitis in many parts of the world. The pathogen affects cattle, goats and sheep; however, infection of cattle is of primary importance due to its impact on the dairy industry, through welfare issues for affected animals, and also because of the significant financial impact on producers. As a species, *S. uberis* is highly-heterogenous; it is biochemically and physiologically ill-defined, and is serologically heterogenous (Hardie, 1986). Furthermore, there is evidence of genetic heterogeneity, driven predominantly through horizontal gene transfer (Coffey et al., 2006). Originally, DNA-DNA hybridization studies suggested the existence of two related *S. uberis* genotypes (designated types I and II) (Garvie & Bramley, *Journal of Applied Microbiology*, vol. 46, issue 2, pp. 295-304, 1979; Farrow et al., *Syst. Appl. Microbiol.*, vol. 5, pp. 467-482, 1984), both associated with the bovine host and a cause of mastitis. Type II *S. uberis* was later re-classified as *Streptococcus parauberis* (Williams and Collins, 1990), which is also increasingly found as a cause of disease in fish; significantly, phylogenetic studies have since shown the two species to be related (Nho et al., 2011), and hence they are likely to share conserved portions of genome.

It is, in part, due to the heterogeneity of the *S. uberis* population that efforts to develop an effective vaccine have been unsuccessful. This is because *S. uberis* antigens which have been shown to have promise as vaccines have not always been found to be conserved amongst the broader population.

It is an object of the present invention to provide antigens which are conserved among strains of *S. uberis* and which may have use or be exploited, in vaccines and methods of diagnosis, detection and/or identification.

SUMMARY OF THE INVENTION

The present invention is based upon the identification of a number of antigens derived from a species of the genus *Streptococcus*, which can be used to raise immune responses in animals—particularly those animals susceptible or predisposed to infection by (or with) the *Streptococcus* species.

The antigens provided by this invention may be exploited to provide compositions and vaccines for raising protective immune responses in animals—the protective immune responses serving to reduce, prevent, treat or eliminate certain *Streptococcus* infections as well as diseases and/or conditions caused or contributed to thereby.

In a first aspect, the invention provides one or more *Streptococcus uberis* antigen(s) or a fragment or fragments thereof, for use in raising an immune response in an animal.

*Streptococcus uberis* is a Gram-positive non-motile coccus. It can infect the bovine mammary gland where it can cause mastitis, an inflammatory disease—indeed, infection with *S. uberis* is one of the major causes of bovine mastitis worldwide. *S. uberis* can be detected in faeces and isolated from environments (for example pasture and/or bedding materials) populated by cattle. It has been placed within the pyogenic cluster, a large grouping containing the human pathogens *Streptococcus pyogenes*, the zoonotic *Streptococcus agalactiae* and a number of animal pathogens occupying diverse ecological niches including *Streptococcus equi* and *Streptococcus canis*.

*Streptococcus uberis* is a highly-heterogeneous species but despite this, the inventors have discovered antigens which are conserved in different *S. uberis* strains. That is to say, while the antigens of this invention may be derived or obtained from a single *S. uberis* strain, they may protect animals against infections and/or diseases caused or contributed to different (heterologous) *Streptococcus uberis* strains. Thus the antigens disclosed herein may be used to facilitate the detection or identification of one, two or more different *S. uberis* strains. Furthermore, vaccine compositions of this invention (comprising one or more of the disclosed antigens) may be used to raise immune responses which are protective against infections, diseases and/or conditions caused any one ormore of a number of different *S. uberis* strains. The inventors have noted that the antigens provided by this invention may also be used to protect animals against infections (or diseases) caused or contributed to by other *Streptococcus* sp., including, for example, infections, diseases and/or conditions caused or contributed to by (but not limited to) *Streptococcus parauberis, S. agalactiae* and *Streptococcus dysgalactiae*.

The antigens described herein may find application in the detection, identification and/or diagnosis of infections, diseases and/or conditions with a Streptococcal (including, but not limited to, *S. uberis, S. parauberis, S. agalactiae* and *S. dysgalactiae*) aetiology.

For convenience, each of the specific *Streptococcus* species and strains relevant to this invention shall be collectively referred to under the general term "*Streptococcus*" or "streptococcal". Moreover, it should be understood that references to *S. uberis* include all related *S. uberis* strains and variants.

An immune response which protects against infection by/with a pathogen or against certain diseases or conditions, may be referred to as a 'protective response'. Therefore, in the context of this invention, the immune responses elicited by the antigens described herein may be regarded as 'protective' immune responses.

The antigens provided by this invention are immunogenic or antigenic in that they elicit host immune responses; the precise nature of the response (humoral and/or cellular for example) may depend on the formulation of the antigen, its route of administration and/or the presence or absence of adjuvant.

The effectiveness of any immune response elicited by the antigens of this invention may be assessed relative to the prevalence or rate of the relevant *Streptococcus* based infection/disease among a population of animals not exposed to, contacted with or administered antigens of this invention. One of skill will appreciate that animals not exposed to, contacted with or administered an antigen of this invention may lack a protective immune response and are therefore more susceptible to *Streptococcus* infections and/or diseases.

A second aspect of this invention provides a composition, immunogenic composition or vaccine composition comprising one or more of the *Streptococcus uberis* antigens described herein. The various compositions may be for use in raising an immune response in an animal. In one embodiment, the immune response is a protective response.

In a third aspect, the invention provides the use of one or more *Streptococcus uberis* antigens or a fragment(s) thereof for the manufacture of a medicament or vaccine for use in the treatment and/or prevention of a *Streptococcus uberis* infection and/or a disease or condition caused thereby or associated therewith.

In a fourth aspect, the invention provides a method of raising an anti-*Streptococcus uberis* immune response in an animal, said method comprising the step of administering to an animal, an amount of one or more *Streptococcus* antigen(s) or fragment(s) thereof, sufficient to induce an anti-*Streptococcus uberis* immune response.

The term "animal" encompasses any animal known to be susceptible to a *Streptococcus* infection, disease or condition. For example, any animal susceptible to infections, diseases or conditions caused or contributed to by *S. uberis, S. parauberis, S. agalactiae* and/or *S. dysgalactiae* (or indeed any strains of any of these) is/are encompassed under the general term "animal" as used herein. For example, the term "animal" may include humans and animals collectively known as avian (birds), piscine (e.g. fish), porcine (pig), bovine (e.g. cattle), caprine (e.g. goats) and/or ovine (e.g. sheep) animals. As such, the invention provides antigens and compositions for use in raising immune responses in human, avian, piscine, caprine, bovine, porcine and/or ovine subjects such as, for example, fish, cattle, sheep and goats.

Diseases and/or conditions caused or contributed to by *Streptococcus* (including for example *S. uberis* and *S. dysgalactiae*) include clinical and sub-clinical cases of mastitis. As such, the antigens provided by this invention may be used to raise immune responses in animals which are susceptible, predisposed and/or prone to developing (streptococcal based) mastitis, said responses being protective against the development of mastitis. For example, the invention may be used to raise immune responses in human, porcine, bovine, caprine and/or ovine animals, said responses being protective against the development of mastitis.

In view of the above, this invention provides:
(i) *Streptococcus uberis* antigens and compositions, vaccines and medicaments comprising the same; and (ii) methods exploiting one or more antigens derived from *Streptococcus uberis*;

for use in raising immune responses in human, avian, piscine, bovine, porcine, caprine and/or ovine animals.

Furthermore, the invention provides:
(i) *Streptococcus uberis* antigens and compositions, vaccines and medicaments comprising the same; and (ii) methods exploiting one or more antigens derived from *Streptococcus uberis*;

for use in treating mastitis; and/or for use in raising immune responses in human, avian, piscine, bovine, porcine, caprine and/or ovine animals, said responses being protective against the development of mastitis.

It should be understood that all references to "antigen" encompass immunogenic components, proteins or peptides derived from *Streptococcus uberis*. The antigens may comprise cell-surface antigens and/or intracellular antigens. The antigens of this invention may be prepared using recombinant technology (as described later) but may be obtained or purified from *S. uberis* cells and/or cell cultures. For example, *S. uberis* cell-surface antigens may be isolated from *S. uberis* cell-wall preparations.

Specifically, the term "antigen" encompasses the exemplary *Streptococcus uberis* antigens listed as (i)-(xvii) in Table 1 below:

TABLE 1

|     | Locus tag | Protein |
| --- | --- | --- |
| i   | SUB0423 | ferrichrome binding protein |
| ii  | SUB0604 | elongation factor Tu |
| iii | SUB0950 | Lipoprotein |
| iv  | SUB1868 | serine protease |

The *S. uberis* antigens identified in Table 1 are those identified in each of the cell-wall sub-cellular fractions of a number of *S. uberis* strains (as determined by mass spectrometry-based proteomic analysis). Consequently, one or more of these antigens may be exploited in this invention and used in the methods, vaccines and/or compositions described herein. Indeed the inventors have noted that a vaccine based on a combination of all four of the antigens disclosed in Table 1 is particularly effective at raising immune responses in cattle which are protective against infection and/or diseases caused or contributed to by *S. uberis*, including, for example, mastitis.

The target genes of the *S. uberis* antigens shown in Table 1 are shown in Table 2 below.

TABLE 2

| Target gene* |
| --- |
| SUB0423 |
| ferrichrome binding protein |
| YP_002561776 |

TABLE 2-continued

| Target gene* |
| --- |
| SUB0604 |
| elongation factor Tu<br>YP_002561947<br>SUB0950 |
| lipoprotein<br>YP_002562276<br>SUB1868 |
| serine proteinase<br>YP_002563137 |

Table 2a shows Conserved carriage of *Streptococcus uberis* antigen-encoding genes.

| Strain identifica-tion‡ | Country of origin | Species of origin | Gene carriage† | | | |
| --- | --- | --- | --- | --- | --- | --- |
| | | | sub0423 | sub0604 | sub0950 | Sub1868 |
| T1-4 | UK | Bovine | + | + | + | + |
| T1-5 | UK | Bovine | + | + | + | + |
| T1-6 | UK | Bovine | + | + | + | + |
| T1-9 | UK | Bovine | + | + | + | + |
| T1-10 | UK | Bovine | + | + | + | + |
| T1-20 | UK | Bovine | + | + | + | + |
| T1-21 | UK | Bovine | + | + | + | + |
| T1-22 | UK | Bovine | + | + | + | + |
| T1-36 | UK | Bovine | + | + | + | + |
| T1-37 | UK | Bovine | + | + | + | + |
| T1-38 | UK | Bovine | + | + | + | + |
| T1-43 | UK | Bovine | + | + | + | + |
| T1-44 | UK | Bovine | + | + | + | + |
| T1-45 | UK | Bovine | + | + | + | + |
| T1-79 | UK | Bovine | + | + | + | + |
| T1-80 | UK | Bovine | + | + | + | + |
| T1-81 | UK | Bovine | + | + | + | + |
| T2-1 | UK | Bovine | + | + | + | + |
| T2-2 | UK | Bovine | + | + | + | + |
| T2-3 | UK | Bovine | + | + | + | + |
| T2-4 | UK | Bovine | + | + | + | + |
| T2-5 | UK | Bovine | + | + | + | + |
| T2-6 | UK | Bovine | + | + | + | + |
| T2-7 | UK | Bovine | + | + | + | + |
| T2-8 | UK | Bovine | + | + | + | + |
| T2-18 | UK | Bovine | + | + | + | + |
| T2-19 | UK | Bovine | + | + | + | + |
| T2-35 | UK | Bovine | + | + | + | + |
| T2-36 | UK | Bovine | + | + | + | + |
| T2-37 | UK | Bovine | + | + | + | + |
| T2-53 | UK | Bovine | + | + | + | + |
| T2-54 | UK | Bovine | + | + | + | + |
| T2-55 | UK | Bovine | + | + | + | + |
| T2-63 | UK | Bovine | + | + | + | + |
| T2-73 | UK | Bovine | + | + | + | + |
| I2 | Italy | Ovine | + | + | + | + |
| I3 | Italy | Ovine | + | + | + | + |
| I4 | Italy | Ovine | + | + | + | + |
| I5 | Italy | Ovine | + | + | + | + |
| I6 | Italy | Ovine | + | + | + | + |
| I7 | Italy | Ovine | + | + | + | + |
| I8 | Italy | Ovine | + | + | + | + |
| I10 | Italy | Ovine | + | + | + | + |
| I11 | Italy | Ovine | + | + | + | + |
| I13 | Italy | Ovine | + | + | + | + |
| I14 | Italy | Ovine | + | + | + | + |
| I23 | Italy | Bovine | + | + | + | + |
| I24 | Italy | Bovine | + | + | + | + |
| I25 | Italy | Bovine | + | + | + | + |
| I26 | Italy | Bovine | + | + | + | + |
| I34 | Italy | Bovine | + | + | + | + |
| I38 | Italy | Bovine | + | + | + | + |
| I44 | Italy | Bovine | + | + | + | + |
| I45 | Italy | Bovine | + | + | + | + |
| I46 | Italy | Bovine | + | + | + | + |
| I47 | Italy | Bovine | + | + | + | + |
| I48 | Italy | Bovine | + | + | + | + |
| I50 | Italy | Bovine | + | + | + | + |
| 1; 1 | USA | Bovine | + | + | + | + |
| 1; 3 | USA | Bovine | + | + | + | + |
| 1; 4 | USA | Bovine | + | + | + | + |
| 1; 40 | USA | Bovine | + | + | + | + |
| 1; 41 | USA | Bovine | + | + | + | + |
| 2; 13 | USA | Bovine | + | + | + | + |
| 2; 14 | USA | Bovine | + | + | + | + |
| 2; 15 | USA | Bovine | + | + | + | + |
| 2; 21 | USA | Bovine | + | + | + | + |
| 2; 22 | USA | Bovine | + | + | + | + |
| 2; 100 | USA | Bovine | + | + | + | + |
| T1-7 (control) | UK | Bovine | − | − | − | − |

†The genes encoding *S. uberis* proteins previously found to be conserved by mass spectrometric analyses were assessed for carriage, by PCR, among a diverse panel of strains. The nomenclature of the conserved genes is derived from the equivalent open reading frames in the published *S. uberis* 0140J genome, and is as follows: sub0423, ferrichrome-binding protein (accession #YP_002561776); sub0604, elongation factor Tu (accession #YP_002561947); sub0950, lipoprotein (accession #YP_002562276); sub1869, serine protease (accession #YP_002563137). All four genes were found to be present in all *S. uberis* strains, with the exception of sub0604 in 1 strain (1; 42) from the USA.

‡An *Enterococcus* spp. strain (T1-7), isolated from a case of bovine mastitis in the UK, was included as a control, and none of the target genes were found to be present.

In view of the above, the term "antigen" as used herein, encompasses antigens encoded by or comprising/consisting (essentially of) the sequences deposited under each of the accession numbers identified in Table 2. It should be noted that the sequences deposited under each of the accession numbers identified above are derived from a *S. uberis* strain designated 0140J (accession number NC 012044). Thus, while the invention encompasses antigens derived from this *S. uberis* strain, it also encompasses the identical, homologous or othologous antigens present in other Streptococci and/or *S. uberis* strains.

The inventors have recombinantly prepared the *S. uberis* antigens and the sequences of the cloned antigens are provided in Table 3 below. One of skill will appreciate that recombinant sequences may comprise sequences which differ from any corresponding wild type or reference sequences and may comprise, for example, sequences which encode protein or peptide tags. Recombinant sequences may be modified by, for example, the deletion of signal peptide sequences. The sequences presented in Table 3 have a 5'-nucleotide sequence encoding a 6× histidine tag—a tag of this type may be used for purification purposes. Also, some of the sequences presented in Table 3 have been further modified to lack sequences encoding secretion signal peptides present in the corresponding wild type sequences.

TABLE 3

| Recombinant gene sequence | Translated product |
|---|---| rSUB0423 ferrichrome binding protein (SEQ ID NO: 1 and 2)

| Seq 1 | Seq 2 |
|---|---|
| ATGGGCAGCAGCCATCATCATCATCATCAC AGCAGCGGCCTGGTGCCGCGCGGCAGCCAT A TGCTCGAGATGTCACAAAGCACAAAGCAAG AAGATCATAAAACAAAACTATCACAAATGC CAAAGATCTCTGGTTTTACCTATAAAGGGA AGGTACCAGAAAACCCTAAAAGAGTAGTTA GTTTATCTTCAACCTACACCGGTTATTTGG CAAAAGCTCGATATCCCACTAGTTGGAATCA CTTCTTATGATCACAAAAATCCCGTCTTAA AGAAATACATCAAGGATGCTAAAGTTGTCT CTGCAACCGACCTAGAAAGCATTACGGCCT TGGAACCTGATTTAATTATTGTGGGTTCAA ATGAAGAAATATCAGTCAATTAGCTGAAA TCGCTCCCCTTATTTCCATTGAATACCGCA AACATGACTATTTACAGGTATTCTCAGATT TTGGTAAAGTCTTTAACAAAACCAAAGAAA CCGACAAATGGTTACAGGAATGGAAAACAA AAACAGCTTCTTTTGAAAGTGACGTTAAAG CAGTTACAGGTAATAATGCTACCTTTACCA TAATGGGATTATATGAGAAAGATATCTATC TTTTCGGTAAAGATTGGGGTCGTGGTGGTG AAATCATTCACCAAGCCTTCCAATATCAAG CTCCAGAAAAAGTAAAAATGGAGGTTTTCC CAAAAGGCTATTTGTCCATTTCACAAGAAG TTCTTCCAGATTATATTGGTGATTATGTCG TTGTCGCTGCAGAGGATGAAAAAACAGGTT CTTCTCTTTATGAAAGTGACCTTTGGAAAA ATATACCAGCCGTTCAAAAAAATCATGTCA TAAATGTTAATGCGAATACCTTTTATTTCA CTGACCCTCTGTCATTAGAGTATGAATTAA AAACCTTAACGGATGCTATCTTGACTCAGA AAACTCACAACTA | MGSSHHHHHHSSGLVPRGSHMLEMSQSTKQ EDHKTKLSQMPKISGFTYKGKVPENPKRVV SLSSTYTGYLAKLDIPLVGITSYDHKNPVL KKYIKDAKVVSATDLESITALEPDLIIVGS N EENISQLAEIAPLISIEYRKHDYLQVFSDF GKVFNKTKETDKWLQEWKTKTASFESDVKA VTGNNATFTIMGLYEKDIYLFGKDWGRGGE IIHQAFQYQAPEKVKMEVFPKGYLSISQEV LPDYIGDYVVVAAEDEKTGSSLYESDLWKN IPAVQKNHVINVNANTFYFTDPLSLEYELK TLTDAILTQKTHN | rSUB0604 elongation factor Tu (SEQ ID NO: 3 and 4)

| Seq 3 | Seq 4 |
|---|---|
| TGGGCAGCAGCCATCATCATCATCATCACA GCAGCGGCCTGGTGCCGCGCGGCAGCCATA TGCTCGAGATGGCAAAGAAAAATACGATC GTAGTAAACCCCACGTTAACATTGGTACAA TTGGACACGTTGACCACGGTAAAACTCTT TGACAGCTGCAATTACAACTGTACTTGCTC GTCGCTTACCAACTTCAGTTAACCAACCAA AAGATTACGCTTCTATCGATGCTGCTCCAG AAGAGCGCGAACGCGGAATCACTATCAACA CTGCACACGTTGAGTACGAAACTGAAACTC GTCACTATGCCCACATTGATGCCCCAGGAC ACGGACTATGTTAAAAACATGATCACTG GTGCTGCCCAAATGGACGGAGCTATCCTTG TTGTTGCATCAACTGATGGACCAATGCCAC AAACTCGTGAGCACATCCTTCTTTCACGCC AAGTTGGTGTTAAACACCTTATCGTTTTCA TGAACAAAATCGACCTTGTTGACGATGAAG AATTGCTTGAATTAGTTGAAATGGAAATCC GTGACCTTCTTTCAGAATACGATTTCCCAG GTGATGACCTACCAGTTATCCAAGGTTCAG CTCTTAAAGCTCTTGAAGGTGATTCTAAAT ACGAAGACATCATCATGGAATTGATGAAAA CTGCTGATGAGTATATTCCAGAACCAGAAC GTGATACAGACAAACCATTACTTCTTCCAG TCGAAGACGTATTCTCAATCACAGGTCGTG GTACTGTAGCTTCAGGACGTATCGATCGTG GTACTGTTCGTGTCAACGACGAAATTGAAA TCGTTGGTATCAAAGAAGAAACTAAAAAAG CAGTTGTTACTGGTGTTGAAATGTTCCGTA AACAACTTGACGAAGGTCTTGCAGGAGATA ACGTAGGTATCCTTCTTCGTGGTGTTCAAC GTGACGAAATCGAACGTGGACAAGTTATTG CTAAACCAGGTTCAATCAACCCACACACTA AATTCAAAGGTGAAGTTTACATCCTTTCTA | MGSSHHHHHHSSGLVPRGSHMLEMAKEKYD RSKPHVNIGTIGHVDHGKTTLTAAITTVLA RRLPTSVNQPKDYASIDAAPEERERGITIN TAHVEYETETRHYAHIDAPGHADYVKNMIT GAAQMDGAILVVASTDGPMPQTREHILLSR QVGVKHLIVFMNKIDLVDDEELLELVEMEI RDLLSEYDFPGDDLPVIQGSALKALEGDSK YEDIIMELMKTADEYIPEPERDTDKPLLLP VEDVFSITGRGTVASGRIDRGTVRVNDEIE IVGIKEETKKAVVTGVEMFRKQLDEGLAGD NVGILLRGVQRDEIERGQVIAKPGSINPHT KFKGEVYILSKDEGGRHTPFFNNYRPQFYF RTTDVTGSIELPAGTEMVMPGDNVTISVEL IHPIAVEQGTTFSIREGGRTVGSGIVSEIE A |

TABLE 3-continued

| Recombinant gene sequence | Translated product |
|---|---|
| AAGATGAAGGTGGACGTCATACTCCATTCT TCAACAACTACCGTCCTCAATTCTATTTCC GTACAACTGACGTAACAGGTTCAATCGAAC TTCCAGCTGGTACTGAAATGGTAATGCCTG GTGATAACGTGACAATCAGCGTTGAGTTGA TCCACCCAATCGCCGTTGAACAAGGTACTA CTTTCTCAATCCGTGAAGGTGGACGTACTG TTGGTTCAGGTATTGTTTCAGAAATCGAAG CTTAA | |

| rSUB0950 lipoprotein (SEQ ID NO: 5 and 6) | |
|---|---|
| Seq 5 | Seq 6 |
| ATGGGCAGCAGCCATCATCATCATCATCAC AGCAGCGGCCTGGTGCCGCGCGGCAGCCAT ATGCTCGAGATGGATAGCAAAGATGCTAAA ACAGATTTAAAAGCTGCTATTGTTACTGAT ACAGGTGGTGTTGATGATAAATCATTTAAC CAATCTGCTTGGGAAGGTTTAGAAGCTTGG GGTAAAGAAAATGGGCTTAAAAAAGGTGCT GGTTTCGACTACTTCCAATCAAATAGTGAA TCAGAATATGCTACTAATCTTGACACTGCT GTCTCAAGTGGTTATAACGTAGTATATGGA ATCGGATTTGCCCTTAAAGATGCAATTGAT AAAGCTGCTGGTGACAATAGTGATGTTAAC TATATTATCGTTGACGATGTCATCGAAGGA AAAGATAATGTTGCAAGTGTAACTTTTGCG GATAACGAAGCTGCTTATCTTGCTGGTATT GCTGCAGCTAAAACTACAAAAACTAAAGTA GTAGGTTTTGTAGGTGGTATGGAAGGTACT GTTATCACTCGTTTTGAAAAAGGTTTTGAG GCGGGAGTGAAATCAGTTGATGATTCTATC CAAATCAAAGTTGACTACGCTGGATCATTT GGTGATGCTGCTAAAGGTAAAACAATTGCC GCAGCTCAATATGCAGGTGGTGCTGACGTT ATTTATCAAGCCGCTGGTGGTACTGGAGCA GGTGTCTTCAATGAAGCTAAAGCTGTAAAT GAGAAAAAAGATGAAGCTGATAAAGTTTGG GTAATCGGTGTAGACCGTGACCAAAAAGAG GAAGGTAAATACACTTCAAAAGACGGTAAA GAATCTAACTTTGTTCTAGCATCTTCAATT AAACAAGTTGGTAAATCTGTACAACTGATT AACAAACTTGTTACTGATAAAAAATTCCCT GGTGGAAAAACAACTGTTTATGGATTAAAA GATGGTGGTGTTGATATTGCAACAACAAAC CTTTCTGATGATGCTATAAAAGCTGTTAAA GAAGCTAAAGAAAAAATTATTTCTGGCGAT GTAAAAGTTCCTGAAAAATAA | MGSSHHHHHHSSGLVPRGSHMLEMDSKDAK TDLKAAIVTDTGGVDDKSFNQSAWEGLEA WGKENGLKKGAGFDYFQSNSESEYATNLDT AVSSGYNVVYGIGFALKDAIDKAAGDNSDV N YIIVDDVIEGKDNVASVTFADNEAAYLAGI AAAKTTKTKVVGFVGGMEGTVITRFEKGFE AGVKSVDDSIQIKVDYAGSFGDAAKGKTIA AAQYAGGADVIYQAAGGTGAGVFNEAKAVN EKKDEADKVWVIGVDRDQKEEGKYTSKDGK ESNFVLASSIKQVGKSVQLINKLVTDKKFP GGKTTVYGLKDGGVDIATTNLSDDAIKAVK EAKEKIISGDVKVPEK |

| rSUB1868 serine proteinase (SEQ ID NO: 7 and 8) | |
|---|---|
| Seq 7 | Seq 8 |
| ATGGGCAGCAGCCATCATCATCATCATCAC AGCAGCGGCCTGGTGCCGCGCGGCAGCCAT ATGACAAATCTTAATAACCCAACGACACA AGTAAAGTAACCTATAAAAATACTACTAAT ACGACTAAAGCTGTTAAAGTGATTCAAGAT GCAGTTGTTTCTGTAGTTAACTATCAAAAA AATGATTCTTTAAACTCAGCCATGGATATT TTTAGTCAAGGTGATTCATCAACTAAAGAG AATGATGGACTTTCTATTTATAGTGAAGGA TCAGGTGTTATATACAAAAAGATGGTGAT TCTGCATATCTGGTAACCAACAACCACGTA ATAGACAAAGCTGAAAGAATTGAAATTATT TTAGCTGATGGTTCAAAAGTTGTTGGGAAA TTAATTGGTGCTGACACTTATTCTGACCTG GCTGTTGTAAAAATTCTTCAGACAAAATT AAGACTGTAGCTCAGTTTGCAGATTCTTCC AAAATAAACATAGGTGAAGTTGCAATTGCA ATTGGTAGTCCTCTTGGAACAGAATATGCT AATTCCGTAACTGAAGGAATTGTTTCAAGT TTAAGTAGAACAGTAACTTTAAAAAATGAA GAAGGACAAACTGTTTCAACTAATGCCATT CAAACAGATGCTGCTATTAACCCTGGAAAC | MGSSHHHHHHSSGLVPRGSHMTNLNNPTTT SKVTYKNTTNTTKAVKVIQDAVVSVVNYQK NDSLNSAMDIFSQGDSSTKENDGLSIYSEG SGVIYKKDGDSAYLVTNNHVIDKAERIEII LADGSKVVGKLIGADTYSDLAVVKISSDKI KTVAQFADSSKINIGEVAIAIGSPLGTEYA NSVTEGIVSSLSRTVTLKNEEGQTVSTNAI QTDAAINPGNSGGPLINIEGQIIGINSSKI SQSKSSGNAVEGMGFAIPANDVIKIINQLE SKGEVVRPALGISMVNLSDLSTNALDQLKV PKNVTSGIVVAKVVDNMPASGKLEQYDIIT EIDGEEVSSTSDLQSILYGHDINDTVKVTF YRGNDKKSTTIELTKTTKDLEK |

TABLE 3-continued

| Recombinant gene sequence | Translated product |
| --- | --- |
| TCTGGCGGACCTTTAATTAATATTGAAGGA | |
| CAAATTATTGGAATAAACTCTAGCAAAATC | |
| TCACAGTCTAAATCATCTGGAAATGCAGTC | |
| GAAGGAATGGGATTTGCAATTCCAGCTAAT | |
| GACGTTATTAAAATTATTAACCAACTTGAA | |
| AGCAAAGGCGAAGTAGTTCGACCTGCATTA | |
| GGTATTTCAATGGTTAATCTAAGTGATTTA | |
| TCAACAAATGCCCTTGATCAGCTCAAAGTT | |
| CCAAAAAATGTTACTAGTGGTATCGTAGTT | |
| GCTAAAGTCGTAGACAATATGCCTGCCTCA | |
| GGAAAACTTGAACAATATGATATTATCACT | |
| GAAATTGATGGGGAAGAAGTGAGCAGTACA | |
| AGTGATTTACAAAGTATTCTGTATGGGCAT | |
| GATATTAATGATACCGTAAAAGTCACTTTT | |
| TATAGAGGTAATGATAAGAAATCTACTACT | |
| ATTGAATTAACTAAAACTACCAAAGATTTA | |
| GAAAAATAA | |

As such, this invention relates to one or more recombinant forms of any of the *S. uberis* antigens identified in this specification—the recombinant sequences being optionally modified (relative to the corresponding wild type sequence) to include sequences encoding tagging or labelling moieties and or through the deletion of one or more wild type sequences or domains—such as, for example, a sequences or domains encoding a signal peptide.

The invention may further relate to the equivalent or corresponding antigens present in other Streptococcal species, including for example the identical, homologous or orthologous antigens present in *S. agalactiae, S. parauberis* and *S. dysgalactiae*. One of skill will appreciate that sequences encoding the antigens of this invention derived from strains other strains of *S. uberis* may differ in nucleic acid sequence. These sequence differences may arise as a result of the natural variation, mutation(s) and/or (single or multiple) nucleotide polymorphisms that often exist between the genomes of related species. Where the biological function of a particular protein is reliant on a particular amino acid sequence, selective pressure will tend to ensure that only mutations which introduce silent or conservative changes to the encoded protein are retained within the microbial population. Consequently, one of skill will recognise that despite divergence in gene coding sequences, retention of biological function through retention of functional epitopes may occur, even though the sequence of less-important regions of a protein coding sequence may vary greatly between strains within a species and between species.

The *S. uberis* antigens described within this invention may be used to immunise animals in order to raise an immune response that neutralises and/or interferes with/abrogates the function of wild-type proteins produced by *S. uberis* during infection, and in so doing reduce the infective capacity of the pathogen. It therefore follows that the same antigens, or derivatives thereof, may also be used to induce equivalent protective immune responses against pathogens other than *S. uberis*. Indeed, an immune response raised by any of the antigens described herein may offer protection against any pathogen (in particular any other *Streptococcus* species) expressing those antigens.

As is well known in the art, the degeneracy of the genetic code permits substitution of one or more bases in a codon without changing the primary amino acid sequence. Consequently, although the nucleic acid sequences described in this application are known to encode *S. uberis* antigens which elicit immune responses in animals, the degeneracy of the code may be exploited to yield variant nucleic acid sequences which encode the same or similar primary amino acid sequences. Additionally or alternatively, the invention further encompasses sequences which have been codon optimised, perhaps for expression in certain cellular (for example bacterial) systems. As such, the term "antigen" encompasses nucleic acid sequences which encode the amino acid sequences of the *S. uberis* antigens described herein including for example described in Tables 1 and 2. The invention may further extend to cDNA generated from messenger RNA encoding any of the antigens of this invention.

It should be understood that this invention further extends to fragments or portions of the various antigens and sequences disclosed herein. The fragments and/or portions of these antigens and/or sequences may themselves provide or encode antigens which are antigenically/immunogenically similar to the complete or whole *Streptococcus uberis* antigens disclosed herein. Thus the fragments and/or portions of this invention are (at least immunologically) functional in that they are capable of eliciting an immune response which is substantially identical, or similar, to an immune response elicited by the complete antigen from which the fragment is derived. The terms "fragments" and "portions" as applied to the *S. uberis* antigens of this invention, encompass immunogenic and/or antigenic fragments and/or portions, which fragments and/or portions can be used to raise immune responses in animals. Fragments or portions of any of the antigens disclosed herein may elicit protective immune responses in animals and may comprise epitopes capable of eliciting protective immune responses.

A fragment or portion of an antigen provided by this invention may comprise any number of amino acid residues or be encoded by any number of nucleic acid residues. For example, fragments of this invention may encompass from about 5 to about 10 residues to about n−1 residues, wherein "n" is the total number of (amino acid or nucleic acid) residues of a *S. uberis* antigen (or antigen coding sequence) described herein. For example, a fragment or portion of a *S. uberis* antigen may comprise or be encoded by a sequence comprising at least about 10, 15, 20, 25, 30, 35, 40, 45, 50, 75, 100, 150, 200, 250, 300 residues—the upper limit (n−1) depending upon the size (n) of the nucleic acid encoding the complete antigen or the number (n) of amino acid residues comprising the primary sequence of the antigen.

In view of the above, the antigen fragments or portions provided by this invention include fragments and/or portions of any of the sequences identified in Tables 1-3 above.

The term "antigen" may further encompass antigens which exhibit a degree of identity and/or homology to the antigens and/or antigen sequences described herein. By way of example, a homologous or identical sequence provided by this invention may exhibit at least 30%, 35%, 40%, 45%, 50%, 55%, 60%, 65%, 70%, 75%, 80%, 85%, 90%, 95%, 96%, 97%, 98%, 99% homology or identity to the various sequences provided herein—including, for example, any of those sequences identified by the accession numbers in Table 2.

The degree of (or percentage) "homology" between two or more (amino acid or nucleic acid) sequences may be determined by aligning the sequences and determining the number of aligned residues which are identical or which are not identical but which differ by redundant nucleotide substitutions (the redundant nucleotide substitution having no effect upon the amino acid encoded by a particular codon, or conservative amino acid substitutions). Homology may assessed by using the Basic Local Alignment Search Tool (BLAST) (Altschul et al., 1990).

A degree (or percentage) "identity" between two or more (amino acid or nucleic acid) sequences may also be determined by aligning the sequences and ascertaining the number of exact residue matches between the aligned sequences and dividing this number by the number of total residues compared—multiplying the resultant figure by 100 would yield the percentage identity between the sequences. The skilled person will be familiar with the various online alignment tools which can be used to determine the degree or percentage identity between two or more amino acid/nucleic acid sequences. For example, the following sites offer suitable alignment tools: ebi.ac.uk/Tools/psa/ and ebi.ac.uk/Tools/msa/clustalw2/.

As with the antigenic fragments and/or portions provided by this invention, any antigens encoded by or comprising/consisting (essentially of) sequences which exhibit homology and/or identity to the sequences described in this application may be immunogenic and suitable for raising immune responses in animals, wherein the immune responses neutralise one or more S. uberis antigens and/or are protective against S. uberis infection and/or diseases and/or conditions caused or contributed to thereby.

A variant, derivative or mutant antigen of this invention may comprise or be encoded by, a nucleic acid or amino acid sequence which comprises one or more nucleotide and/or amino acid substitutions, inversions, additions and/or deletions relative to a reference sequence. A reference sequence may be any of the sequences described in this application. The term "substitution" may encompass one or more conservative substitution(s). One of skill in this field will understand that the term "conservative substitution" is intended to embrace the act of replacing one or more amino acids of a protein or peptide with an alternate amino acid with similar properties and which does not substantially alter the physico-chemical properties and/or structure or function of the native (or wild-type) protein.

Examples of such conservative substitutions are presented in Table 4.

TABLE 4

Conservative amino acid substitutions

| Residue | Abbreviation | Conservative substitutions |
| --- | --- | --- |
| Alanine | Ala | Ser |
| Arginine | Arg | Lys |
| Asparagine | Asn | Gln, His |
| Aspartic acid | Asp | Glu |
| Cysteine | Cys | Asn |
| Glutamic adic | Glu | Ser |
| Glutamine | Gln | Asp |
| Glycine | Gly | Pro |
| Histidine | His | Asn, Gln |
| Isoleucine | Ile | Leu, Val |
| Leucine | Leu | Ile, Val |
| Lysine | Lys | Arg, Gln |
| Methionine | Met | Leu, Ile |
| Phenylalanine | Phe | Met, Leu, Tyr |
| Proline | Pro | |
| Serine | Ser | Thr, Gly |
| Threonine | Thr | Ser, Val |
| Tryptophan | Trp | Tyr |
| Tyrosine | Tyr | Trp, Phe |
| Valine | Val | Ile, Leu |

One of skill will appreciate that the antigens described herein may comprise domains and regions (or epitopes) which represent the immunogenic or active parts. The immunogenic of active parts of an antigen of this invention are those domains, regions or epitopes which are capable of inducing an immune response in the relevant animal. Therefore, antigens for use in this invention may comprise synthetic or recombinant constructs or fusions which comprise these immunogenic or active regions, domains or epitopes. For example, antigens for use in this invention may comprise sequences which exhibit at least 30%, 35%, 40%, 45%, 50%, 55%, 60%, 65%, 70%, 75%, 80%, 85%, 90%, 95%, 96%, 97%, 98%, 99% or 100% homology or identity (as defined above) to the sequences of the active or immunogenic (epitope containing) domains or regions of the antigens described herein, including, for example, those sequences identified by accession number in Table 2.

In the context of this invention, a variant, derivative or mutant S. uberis antigen may comprise or be encoded by a variant, derivative or mutant sequence which, when compared to a reference sequence (such as for example a wild-type S. uberis sequence or a sequence of or encoding any of the specific S. uberis antigens presented above, is found to contain one or more amino acid/nucleotide substitutions, additions, deletions and/or inversions.

An antigen which may be regarded as a derivative of the S. uberis antigens described herein may further comprise one or more features (for example epitopes or domains) of an S. uberis antigen fragment or mutant, variant or derivative described herein, optionally in combination with one or more modifications to the structure of the antigen or one or more of the amino acid residues thereof.

As with the antigenic fragments and/or portions provided by this invention, the mutant, variant and/or derivative sequences described herein may be immunogenic and suitable for raising immune responses in animals, wherein the immune responses neutralise one or more S. uberis antigens and/or are protective against S. uberis infection and/or diseases and/or conditions caused or contributed to thereby.

In view of the above, the present invention relates to:
(a) S. uberis:
(i) lipoprotein (acc No: YP_002562276)
(ii) serine proteinase (acc No: YP_002563137)

(iiii) ferrichrome binding protein: (acc No: YP_002561776)

(iv) elongation factor Tu: (acc No: YP_002561947) (b) antigens or proteins having or encoded by sequences comprising, consisting or consisting essentially of sequences which exhibit at least about 60% identity to the sequences described in this application (that is, for example, the sequences disclosed by reference to deposited accession numbers) and/or as (i)-(iv) above;

(c) antigens or proteins having or encoded by or comprising, consisting or consisting essentially of sequences which represent variant, derivative or mutant sequences of those sequences encoding the *S. uberis* antigens described herein and/or as (i)-(iv) above; and (d) antigens or proteins having or comprising sequences corresponding to the immunogenic domains of the antigens described herein (for example, the antigens presented in Table 2) and/or as (i)-(iv) above.

Antigens of this type may comprise sequences which share about 60% to about 100% sequence identity with the immunogenic domains of any of these antigens.

It will be appreciated that the *S. uberis* antigens described in this application may be obtained by direct purification from *S. uberis* cultures and/or protein/membrane preparations thereof. Additionally or alternatively, the antigens of this invention may be generated recombinantly.

PCR techniques may be exploited to selectively amplify the appropriate antigen (for example *S. uberis* antigen) gene sequences from a variety of sources including, for example, stored *Streptococcus* and/or *S. uberis* isolates, clinical isolates, diseased material and the like. Cloned antigen sequences may be introduced into a vector (such as a plasmid or expression cassette). In one embodiment, the vector may further comprise a nucleotide sequence of a tag or label to assist in protein purification procedures.

A host cell may be transformed or transfected with a vector and maintained under conditions suitable to induce expression of an antigen (for example a *S. uberis* antigen) gene sequence and production of recombinant antigen. Prokaryotic or eukaryotic cells, such as, for example bacterial, plant, insect, mammalian and/or fungal cells, may be transformed or transfected with one or more of the vectors described herein. One of skill in this field will be familiar with the techniques used to introduce heterologous or foreign nucleic acid sequences, such as expression vectors, into cells and these may include, for example, heat-shock treatment, use of one or more chemicals (such as calcium phosphate) to induce transformation/transfection, the use of viral carriers, microinjection and/or techniques such as electroporation. Further information regarding transformation/transfection techniques may be found in Current Protocols in Molecular Biology, Ausuble, F. M., ea., John Wiley & Sons, N.Y. (1989) which is incorporated herein by reference. In one embodiment, the host cell is a bacterial cell such as, for example, an *Escherichia coli* cell.

Techniques used to purify recombinant proteins generated in this way are known and, where the recombinant protein is tagged or labelled, these may include the use of, for example, affinity chromatography techniques.

In view of the above, this invention may provide expression vectors comprising *S. uberis* antigen gene sequence(s) and host cells transformed therewith.

For convenience all of the antigens, including the *S. uberis* antigens (both purified and/or recombinant forms) described herein, shall hereinafter be collectively referred to as "antigens" or "*S. uberis* antigens". Moreover, references to specific antigens and/or *S. uberis* antigens should be taken to include (immunogenic) fragments or portions derived therefrom (as described above) as well as any mutants, variants and derivatives thereof and/or antigens exhibiting a degree of homology/identity thereto.

The inventors have discovered that animals (in particular bovine, porcine caprine and/or ovine animals) administered one or more of the *S. uberis* lipoprotein (acc No: YP_002562276), *S. uberis* serine proteinase (acc No: YP_002563137), *S. uberis* ferrichrome binding protein: (acc No: YP_002561776) and/or *S. uberis* elongation factor Tu: (acc No: YP_002561947) antigens, elicit particularly effective protective immune responses.

As such, this invention may provide immunogenic and/or vaccine compositions comprising one or more of the *S. uberis* lipoprotein (acc No: YP_002562276), *S. uberis* serine proteinase (acc No: YP_002563137), *S. uberis* ferrichrome binding protein: (acc No: YP_002561776) and/or *S. uberis* elongation factor Tu: (acc No: YP_002561947).

In one embodiment, any of the antigens or *S. uberis* antigens described herein may be admixed with one or more other components, such as another polypeptide and/or an adjuvant, diluent or excipient. Additionally, or alternatively, vaccines or vaccine compositions provided by this invention may, for example, contain viral, fungal, bacterial or other parasite antigens used to control other diseases/infections or infestations. For example, the vaccine or vaccine composition may be included within a multivalent vaccine, which includes antigens against other ovine or bovine pathogens/diseases.

The term "adjuvant" generally refers to any material that increases the humoral or cellular immune response to an antigen. Adjuvants are used to accomplish two objectives: They slow the release of antigens from the injection site, and they enhance stimulation of the immune system. The addition of an adjuvant may permit the use of a smaller dose of antigen to stimulate a similar immune response, thereby reducing the production cost of the vaccine. Thus, the effectiveness of some injectable medicinal agents may be significantly increased when the agent is combined with an adjuvant.

In view of the above, the present invention may provide a vaccine composition comprising a *S. uberis* antigen and an adjuvant formulation.

The *S. uberis* antigen component of a vaccine composition of this invention may comprise, consist essentially of or consist of a *S. uberis* ferrichrome binding protein, *S. uberis* elongation factor Tu, *S. uberis* lipoprotein, *S. uberis* serine proteinase, an immunogenic fragment of any of these or a combination thereof.

The vaccine compositions of this invention may comprise, consist essentially of or consist of *S. uberis* ferrichrome binding protein, *S. uberis* elongation factor Tu, *S. uberis* lipoprotein, *S. uberis* serine proteinase, an immunogenic fragment of any of these or a combination thereof optionally in combination with an adjuvant.

The vaccine of this invention may comprise, consist essentially of or consist of a *S. uberis* ferrichrome binding protein, *S. uberis* elongation factor Tu, *S. uberis* lipoprotein, *S. uberis* serine proteinase, an immunogenic fragment of any of these or a combination thereof optionally in combination with an adjuvant for use in treating mastitis or raising an immune response which is protective against mastitis. The vaccine may be further exploited in methods of treating subjects in need thereof, the method comprising administering an immunologically effective amount of the vaccine to the subject. The subject may be a bovine subject or any subject (bovine or otherwise) predisposed or susceptible to contracting or developing mastitis. The subject may be suffering from mastitis. The subject may be predisposed or susceptible to contracting or developing a *S. uberis* infection or a *S. uberis* associated disease and/or condition.

The adjuvant (optionally to be used with any of the vaccine formulations disclosed herein) may be any suitable adjuvant. The adjuvant may not be an adjuvant formulation comprising, consisting essentially of or consisting of an oily phase and an aqueous phase, wherein the oily phase comprises at least 50% of the formulation v/v, wherein said formulation comprises at least one of monophosphoryl lipid A (MPL-A) or an analog thereof and an immunostimulatory oligonucleotide, with provisos that a) if said immunostimulatory oligonucleotide is absent, then the formulation comprises a poly I:C, a glycolipid, and, optionally, a quaternary amine; or a polycationic carrier; and b) if said monophosphoryl lipid A (MPL-A) or the analog thereof is absent, then the formulation comprises a source of aluminum, and, optionally, a polycationic carrier.

Polypeptides which may be used in conjunction with any or all of the antigens of this invention may include, for example polypeptides which are fused, bound or conjugated to the *S. uberis* antigens described herein. Thus this invention further encompasses fusions comprising the *S. uberis* antigens described herein. The fusions may be internal fusions where a peptide or protein is embedded into the amino acid sequence of an antigen of this invention. Additionally or alternatively, the fusions may comprise C- or N-terminal fusions in which a peptide or protein is fused to the N- and/or C-terminal portion of a *S. uberis* antigen of this invention. In some cases, the *S. uberis* antigens (or the fragments thereof) of this invention may take the form of haptens—that is to say they are small molecules which elicit immune responses only when attached to a large carrier such as a peptide or protein. In some cases, the carrier protein or peptide may not elicit an immune response by itself. Where the *S. uberis* antigen is a hapten, it may be fused, combined, bound or conjugated with or to a carrier protein or peptide so as to enhance or increase its ability to raise an immune response in an animal.

In a further aspect, the present invention provides an animal population treated, vaccinated and/or immunised with an antigen or antigen(s), vaccine or composition of this invention. For example, the invention provides treated, vaccinated or immunised human, avian, piscine, bovine, porcine, caprine and/or ovine populations; for example, the invention may provide farmed populations of birds, fish, cattle, pigs sheep and/or goats which have been treated, vaccinated and/or immunised with an antigen or antigen(s), vaccine or composition described herein. As stated, a vaccine or composition of this invention may comprise one or more of the *S. uberis* antigens described herein optionally in combination with one or more other antigens and/or adjuvants.

The compositions, including the vaccine compositions, provided by this invention may be formulated as sterile pharmaceutical compositions comprising one or more of the antigens described herein and a pharmaceutical excipient, carrier or diluent. These composition may be formulated for oral, topical (including dermal and sublingual), intramammary, parenteral (including subcutaneous, intradermal, intramuscular and intravenous), transdermal and/or mucosal administration.

The (vaccine) compositions described herein, may comprise a discrete dosage unit and may be prepared by any of the methods well-known in the art of pharmacy. Methods typically include the step of bringing into association one or more of the *S. uberis* antigens described herein with liquid carriers or finely-divided solid carriers or both.

Compositions (the term "composition" including immunogenic and vaccine compositions of this invention), suitable for oral administration, wherein the carrier is a solid, are most preferably presented as unit dose formulations such as boluses, capsules or tablets each containing a predetermined amount of one or more of the *S. uberis* antigens of this invention. A tablet may be made by compression or moulding, optionally with one or more accessory ingredients. Compressed tablets may be prepared by compressing in a suitable machine an active compound (for example one or more *S. uberis* antigen(s)) in a free-flowing form such as a powder or granules optionally mixed with a binder, lubricant, inert diluent, lubricating agent, surface-active agent or dispersing agent. Moulded tablets may be made by moulding an active compound with an inert liquid diluent. Tablets may be optionally coated and, if uncoated, may optionally be scored. Capsules may be prepared by filling an active compound, either alone or in admixture with one or more accessory ingredients, into the capsule shells and then sealing them in the usual manner. Cachets are analogous to capsules wherein an active compound together with any accessory ingredient(s) is sealed in a rice paper envelope. An active compound may also be formulated as dispersible granules, which may for example be suspended in water before administration, or sprinkled on food. The granules may be packaged, for example in a sachet. Formulations suitable for oral administration wherein the carrier is a liquid may be presented as a solution or a suspension in an aqueous or non-aqueous liquid, or as an oil-in-water liquid emulsion.

Compositions suitable for oral administration include controlled release dosage forms, for example tablets wherein an active compound (for example one or more *S. uberis* antigens) is formulated in an appropriate release-controlling matrix, or is coated with a suitable release-controlling film. Such compositions may be particularly convenient for prophylactic use.

Composition and vaccine compositions formulated for parenteral administration include sterile solutions or suspensions of an active compound (for example one or more *S. uberis* antigens) in aqueous or oleaginous vehicles. Compositions of this invention, including vaccine and/or immunogenic compositions, may comprise, or further comprise cryoprotectant compounds or compositions, preservative(s), antibiotics, adjuvants and the like.

Injectable compositions and vaccines may be adapted for bolus injection or continuous infusion. Such preparations are conveniently presented in unit dose or multi-dose containers, which are sealed after introduction of the formulation until required for use. Alternatively, an active compound (for example one or more *S. uberis* antigens) may be in powder form that is constituted with a suitable vehicle, such as sterile, pyrogen-free water or phosphate buffered saline PBS before use.

Compositions comprising one or more antigens or *S. uberis* antigens of this invention may also be formulated as long-acting depot preparations, which may be administered by intramuscular injection or by implantation, e.g. subcutaneously or intramuscularly. Depot preparations may include, for example, suitable polymeric or hydrophobic materials, or ion-exchange resins. They may also include preparations or adjuvants known to enhance the affinity and/or longevity of an animal (for example bovine, ovine or caprine) immune response, such as single or double emulsions of oil in water. Such long-acting compositions are particularly convenient for prophylactic use.

Compositions suitable (or formulated) for mucosal administration include compositions comprising particles for aerosol dispersion, or dispensed in drinking water. When dispensed, such compositions should desirably have a particle diameter in the range 10 to 200 microns to enable retention in, for example, the nasal cavity; this may be achieved by, as appropriate, use of a powder of a suitable particle size or choice of an appropriate valve. Other suitable compositions include coarse powders having a particle diameter in the range 20 to 500 microns, for administration by rapid inhalation through the nasal passage from a container held close up to the nose, and nasal drops comprising 0.2 to 5% w/v of an active compound in aqueous or oily solution or suspension.

It should be understood that, in addition to the carrier ingredients mentioned above, the various compositions described herein may include an appropriate one or more additional (pharmaceutically acceptable) carrier ingredients such as diluents, buffers, flavouring agents, binders, surface active agents, thickeners, lubricants, preservatives (including anti-oxidants) and the like, and substances included for the purpose of rendering the formulation isotonic with the blood of the intended recipient.

Pharmaceutically acceptable carriers are well known to those skilled in the art and include, but are not limited to, 0.1 M and preferably 0.05 M phosphate buffer or 0.8% saline. Additionally, pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Preservatives and other additives may also be present, such as, for example, antimicrobials, antioxidants, chelating agents, inert gases and the like.

Compositions suitable for topical formulation may be provided, for example, as gels, creams or ointments.

Compositions for veterinary use may conveniently be in either powder or liquid concentrate form. In accordance with standard veterinary formulation practice, conventional water-soluble excipients, such as lactose or sucrose, may be incorporated in the powders to improve their physical properties. Thus, particularly suitable powders of this invention comprise 50 to 100% w/w and preferably 60 to 80% w/w of the active ingredient(s) (for example one or more *S. uberis* antigens) and 0 to 50% w/w and preferably 20 to 40% (w/w) of conventional veterinary excipients. These powders may either be added to, for example, animal feed—perhaps by way of an intermediate premix, or diluted in animal drinking water.

Liquid concentrates of this invention suitably contain one or more antigens or *S. uberis* antigens and may optionally further include an acceptable water-miscible solvent for veterinary use, for example polyethylene glycol, propylene glycol, glycerol, glycerol formal or such a solvent mixed with up to 30% (v/v) of ethanol. The liquid concentrates may be administered to the drinking water of animals.

In addition to providing *S. uberis* antigens for use in raising immune responses in animals, the present invention may also provide polyclonal and/or monoclonal antibodies (or antigen binding fragments thereof) that bind (or have affinity or specificity for) any of the antigens or *S. uberis* antigens provided by this invention. Production and isolation of polyclonal/monoclonal antibodies specific for protein/peptide sequences is routine in the art, and further information can be found in, for example "Basic methods in Antibody production and characterisation" Howard & Bethell, 2000, Taylor & Francis Ltd. Such antibodies may be used in diagnostic procedures, to, for example detect or diagnose *S. uberis* infection/infestations in animal (for example bovine, caprine or ovine) species, as well as for passive immunisation.

The present invention further provides a vaccine for use in preventing or controlling *Streptococcus* infections and/or associated diseases and/or conditions. The vaccines may find particular application in preventing or controlling mastitis (namely mastitis with a Streptococcal aetiology). The vaccines provided by this invention may be used to prevent or control *S. uberis* infections and/or associated diseases. The vaccines may also be used to prevent or control streptococcal infections and/or associated diseases in human, avian, piscine, bovine, porcine, ovine and/or caprine hosts. The vaccine may be a polypeptide or polynucleotide vaccine—the polypeptides and/or polynucleotides providing, or encoding, one or more of the (*S. uberis*) antigens described herein.

The invention further provides a method for immunising an animal against an infection or disease caused or contributed to by a *Streptococcus* species, said method comprising the step of administering a vaccine of the invention to a subject in need thereof. Subjects in need thereof may be animals suffering (or suspected of suffering from) a streptococcal infection or disease and/or animals regarded as susceptible or predisposed to such diseases and/or infections. For example, the invention provides methods of immunising a human, an avian, a piscine, a caprine, a porcine, an ovine and/or bovine subject against *S. uberis* infection/infestation and associated diseases, said method comprising the step of administering a vaccine of the invention to the human, avian, piscine, caprine, porcine, ovine or bovine subject. A subject in need thereof may be any animal subject suffering from mastitis.

The antigens and/or vaccines of this invention may be exploited in the immunisation of animals against mastitis, wherein the mastitis results from, is associated with or is caused or contributed to by, a *Streptococcus* species (for example *S. uberis* or *S. dysgalactiae*) or infection therewith.

The antigens of this invention may find further application as the basis of diagnostic or identification/detection tests for various *Streptococcus* species/strains including any species or strain which expresses any of the antigens described herein. For example, the antigens provided by this invention may be applied to the detection, identification and/or diagnosis of *S. uberis, S. agalactiae, S. dysgalactiae*, and *S. parauberis* infections, and/or diseases caused thereby or associated therewith. The antigens may also be used in methods for detecting the presence of streptococci in samples.

Thus, an aspect of this invention may provide an (in vitro) method of detecting, identifying and/or diagnosing a *streptococcus* spp., *S. uberis, S. agalactiae, S. dysgalactiae* and/or *S. parauberis* infection or a disease caused thereby or associated therewith, the method comprising detecting a level of one or more of the antigens described herein in a sample and/or detecting a level of an antibody with specificity for one or more of the antigens described herein, in a sample.

A sample may comprise any biological fluid or tissue including, for example, whole blood; red blood cells, serum; plasma; saliva; sweat; semen; milk, (disease) tissue biopsy; tissue scraping; tissue/organ wash/lavage; and/or faecal preparations. The term "sample" may further extend to samples of animal feed/drink, bedding or field samples such as soil and grass.

Methods of detecting levels of antigen or antibody in a sample may comprise immunological methods. For example, methods of detecting levels of antigen or antibody may exploit enzyme-linked immunosorbant assay (ELISA) techniques. By way of example, one or more of the antigens described herein may be immobilised to a substrate and the immobilised antigen(s) used to probe a sample for the presence of antibodies reactive thereto. After a suitable period of incubation between the immobilised antigen and the sample, the presence or absence of antibodies may be detected by means of a secondary binding agent (for example antibody) optionally conjugated to a detectable moiety, with specificity for antibodies generated by the relevant species—for example bovine, caprine or ovine antibodies. The presence of antibodies may indicate the presence of a Streptococcus (for example S. uberis) and/or an infection therewith or a Streptococcus (for example an S. uberis) associated disease or condition.

Alternatively, binding agents or antibodies with specificity to one or more of the antigens described herein may be immobilised onto a substrate. The substrate may then be used to probe a sample for the presence of one or more antigens to which the binding agents or antibodies bind. After a suitable period of incubation between the sample and the immobilised antibody, the substrate may be contacted with a secondary binding agent or antibody with specificity for the relevant antigens. The secondary binding agent or antibody may be conjugated to a detectable moiety. Alternatively, the immobilised binding agent:antigen:binding agent complexes may be further probed with a tertiary binding agent or antibody capable of binding to the secondary binding agent. The tertiary binding agent may be conjugated to a detectable moiety.

Other immunological techniques such as immunohistochemical staining may exploit binding agents (for example antibodies/conjugated antibodies) with specificity for one or more of the antigens described herein, to detect the presence or absence of Streptococci (for example S. uberis) antigens in a sample, for example a tissue sample.

Molecular methods may also be used to detect the presence of any of the antigens described herein (for example S. uberis antigens) in a sample. For example, primer sequences designed to amplify sequences encoding one or more of the (S. uberis) antigens of this invention may be used to probe samples for the presence of the relevant (for example S. uberis) nucleic acid. Further information regarding these (PCR-based) techniques may be found in, for example, PCR Primer: A Laboratory Manual, Second Edition Edited by Carl W. Dieffenbach & Gabriela S. Dveksler: Cold Spring Harbour Laboratory Press and Molecular Cloning: A Laboratory Manual by Joseph Sambrook & David Russell: Cold Spring Harbour Laboratory Press.

The present invention also extends to kits comprising reagents and compositions suitable for identifying or detecting the presence or absence of Streptococci (including S. uberis, S. dysgalactiae and/or S. parauberis) and/or diagnosing or detecting streptococci (including S. uberis, S. dysgalactiae and/or S. parauberis) infections or diseases. For example, depending on whether or not the kits are intended to be used to identify or detect streptococci and/or levels of antigen or antibodies thereto in samples, the kits may comprise substrates having antigens of this invention or agents capable of binding the same, bound thereto. In addition, the kits may comprise agents capable of binding the relevant (for example S. uberis) antigens. Thus, where the kit is to be used to identify levels of S. uberis antigen in samples, the kit may comprise an agent capable of binding the relevant S. uberis antigen. The kit may comprise specifically raised polyclonal antibodies or monoclonal antibodies—the antibodies having specificity for antigens provided by this invention. Where the kits are intended to diagnose or detect streptococci or streptococcal diseases in specific animals (for example human, avian, porcine, piscine, bovine, caprine and/or ovine animals) the kits may comprise binding agents or antibodies capable of binding immunoglobulin from the relevant species. The antibodies may be conjugated to detectable moieties. Kits for use in detecting the expression of genes encoding any of the antigens of this invention may comprise one or more oligonucleotides/primers for detecting/amplifying/probing the relevant antigen-encoding sequences. The kits may also comprise other reagents to facilitate, for example, sequencing, PCR and/or RFLP analysis. All kits described herein may further comprise instructions for use.

The present invention will now be described in detail with reference to the following Examples:

EXAMPLE 1

Materials, Methods & Results

Bacterial Strains and Culture Conditions

The reference strain, Streptococcus uberis 0140J (ATCC BAA-854) was used in this study, in addition to a further 69 S. uberis clinical isolates derived from cases of bovine and ovine mastitis from distinct farms within the UK, Italy and the USA, and comprised strains which either persisted or were cured following antibiotic therapy. For routine culture, bacteria were propagated in Brain Heart Infusion (BHI) broth or agar. Bacteria for inclusion in proteomic analyses were propagated in a defined medium to provide a suitable growth environment lacking medium-derived peptides that would interfere with a mass spectrometric approach. Irrespective of the medium used, cultures were incubated static at 37° C.

Analysis of S. uberis Cell-Wall and Cell-Wall-Associated Proteins

Twenty S. uberis strains, including the reference strain, were assessed in a proteomic analysis to identify putatively conserved proteins. Bacteria were propagated in 50 ml volumes to late exponential growth-phase; growth curves for each strain had been generated in a prior experiment, whereby growth was measured in the defined medium over time (data not shown). Bacterial cells were harvested by centrifugation at 30,000×g for 20 m and washed twice with ice-cold PBS. Subsequently, in microcentrifuge tubes, the bacterial pellets were carefully re-suspended in 0.5 ml of PBS containing 40% (w/v) sucrose, 1 mM DTT and 20 µg sequencing grade modified trypsin (Promega). Proteolytic digestion of cells to liberate cell-wall and cell-wall-associated proteins was carried out for 2 h at 37° C. with gentle shaking. Subsequently, the digestion mixtures were centrifuged at 30,000×g for 10 m to pellet cells, and each supernatant was transferred to a fresh microcentrifuge tube. Incubation of supernatants was continued overnight at 37° C., then each was filtered through a 0.45 µm Spin-X centrifuge tube filter (Corning) and stored in a refrigerator until required.

Mass Spectrometric Analysis

Peptide mixtures were cleaned using a C5-Reversed Phase HPLC column. Subsequently, filtered samples were subjected to liquid chromatography-electrospray ionisation-tandem mass spectrometry (LC-ESI-MS/MS) analysis. Liquid chromatography was performed using an UltiMate® 3000 nano-HPLC system (Dionex) comprising a WPS-3000-well plate micro auto-sampler, a FLM-3000 flow manager and column compartment, a UVD-3000 UV detector, an LPG-3600 dual-gradient micro-pump and an SRD-3600 solvent rack controlled by Chromeleon™ chromatography software (Dionex: www1.dionex.com). A micro-pump flow rate of 246 µl min$^{-1}$ was used in combination with a cap-flow splitter cartridge, affording a 1/82 flow split and a final flow rate of 3 µl min$^{-1}$ through a 5 cm×200 µm ID monolithic reversed-phase column (Dionex/LC Packings) maintained at 50° C. Samples of 1-4 µl were applied to the column by direct injection. Peptides were eluted by the application of a 15 min linear gradient from 8-45% solvent B (80% (w/v) acetonitrile, 0.1% (v/v) formic acid) and directed through a 3 nl UV detector flow cell. LC was interfaced directly with an Esquire HCTplus™ 3-D high capacity ion trap mass spectrometer (Bruker Daltonics) via a low-volume (50 µl min$^{-1}$ maximum) stainless steel nebuliser (Agilent) and ESI. Parameters for tandem MS analysis were set as previously described (Batycka et al., *Rapid Communications in Mass Spectrometry*, vol. 20, issue 14, pp. 2074-2080, 2006).

Deconvoluted MS/MS data was submitted to an in-house server running MASCOT (MATRIX SCIENCE), and searched against the fully-annotated *S. uberis* 0140J genome sequence (NC 012004) using the MASCOT search algorithm. To this end, the fixed- and variable-modifications selected were carbamidomethyl (C) and oxidation (M) respectively, and mass tolerance values for MS and MS/MS were set at 1.5 Da and 0.5 Da respectively. Molecular weight search (MOWSE) scores attained for individual protein identifications were inspected manually and considered significant only if two or more peptides were matched for each protein and identified peptide contained an unbroken "b" or "y" ion series of a minimum of four amino acid residues. An in-house software programme was used to process raw MASCOT data and generate non-redundant lists of proteins identified in each of the cell-wall sub-cellular fractions of the 20 *S. uberis* strains. Proteins which were present in 50% or greater of the 20 strains (Table 4a) were considered putative candidate antigens for vaccine development and were subjected to further study.

Assessing Carriage of Candidate Antigen-Encoding Genes Among a Larger Panel of Strains To further appraise the conservation of proteins identified by mass spectrometry, PCR was used to determine the presence/absence of protein-coding sequences within the genomes of the larger panel of *S. uberis* strains. Genomic DNA of 69 *S. uberis* strains (including those strains assessed by mass spectrometry) was extracted from overnight cultures using the DNeasy Blood & Tissue Extraction Kit (Qiagen) as per the manufacturer's instructions for 'hard to lyse' Gram-positive bacteria. Oligonucleotide primer pairs (Table 5) were designed to allow PCR amplification of each of the target genes. PCR was conducted using Taq PCR MasterMix Kit (Qiagen), as per the manufacturer's instructions. Following PCR, amplicons were visualised over UV light following electrophoresis through 1% (w/v) agarose gels containing GelRed. In all cases a PCR product was observed, indicative of the antigen encoding gene being present in each of the analysed strains. Subsequently, selected PCR products were analysed further by sequencing to confirm the identity of the amplified sequences (data not shown).

Based upon the results of proteomic and genomic screening, 4 conserved targets were identified (Tables 4a, 5 and 6) and chosen for further assessment as candidate vaccine antigens.

Production of Recombinant Antigens

Each of the genes were amplified by PCR (as previously) from *S. uberis* 0140J genomic DNA using oligonucleotide primers designed to include appropriate restriction endonuclease recognition sites to facilitate in-frame cloning into the expression plasmid (Table 6). For genes predicted to contain a secretion signal peptide-encoding sequence (as determined using SignalP V.3.0; Bendtsen et al. 2004), each forward primer was designed to anneal, in-frame, immediately after the predicted signal peptide-encoding sequence. PCR amplicons were initially cloned using the TOPO TA Cloning Kit (Life Technologies Corp.). Subsequently, the *S. uberis* genes were cleaved from the TOPO vector using the primer-encoded restriction endonuclease sites; digests were electrophoresed through 1% (w/v) agarose gels, and the desired fragments were excised and purified using the QIAquick Gel extraction Kit (Qiagen). Finally, each *S. uberis* gene was cloned into pET-15b expression plasmid (Novagen), to allow expression of each protein with an N-terminal 6× histidine (his) residue tag to facilitate downstream purification.

TABLE 4a

List of proteins conserved amongst isolates selected by proteomic analysis.

| Locus tag | Protein | Conservation (%) |
|---|---|---|
| SUB0423 | ferrichrome binding protein | 80 |
| SUB0604 | elongation factor Tu | 50 |
| SUB0950 | Lipoprotein | 65 |
| SUB1868 | serine protease | 100 |

TABLE 5

Oligonucleotide primers used for screening *S. uberis* strains.

| Target gene | Sequence (5'- to -3') | |
|---|---|---|
| SUB0423 | Forward primer | GTTCTAGGAGATTAGAATTCA (SEQ ID NO: 9) |
| | Reverse primer | TTTGGTTTGTGTCCGTCATAA (SEQ ID NO: 10) |
| SUB0604 | Forward primer | AGTAAGGTAAAGTTAGACTGT ATTG (SEQ ID NO: 11) |
| | Reverse primer | AGTTGTCTGACTCTAATTGTT AATC (SEQ ID NO: 12) |
| SUB0950 | Forward primer | GTTATTGGCCATAAGGCTA (SEQ ID NO: 13) |
| | Reverse primer | TAAGGTCGCTCCACATTT (SEQ ID NO: 14) |
| SUB1868 | Forward primer | AGGTAATGCCGTGTCTA (SEQ ID NO: 15) |
| | Reverse primer | ATGAATCCGAGGTTGGTA (SEQ ID NO: 16) |

TABLE 6

PCR amplification of candidate antigen-encoding genes.

| Target gene* | Primer name | Restriction site added | Primer sequence (5'- to -3') (SEQ ID NOS: 17-24) |
|---|---|---|---|
| SUB0423 | | | |
| ferrichrome binding protein | SUB0423_NSP_FX | XhoI | CGCGCGCTCGAGATGTCACAAAGCACAAAG |
| YP_002561776 | SUB0423_NSP_RB | BamHI | CGCGCGGGATCCCTAGTTGTGAGTTTTCTG |
| SUB0604 | | | |
| elongation factor Tu | SUB0604_FX | XhoI | CGCGCGCTCGAGATGGCAAAAGAAAAATAC |
| YP_002561947 | SUB0604_R | BamHI | CGCGCGGGATCCTTAAGCTTCGATTTCTGA |
| SUB0950 | | | |
| lipoprotein | SUB0950_NSP_FX | XhoI | CGCGCGCTCGAGATGGATAGCAAAGATGCT |
| YP_002562276 | SUB0950_NSP_RB | BamHI | CGCGCGGGATCCTTATTATTTTTCAGGAACTTT |
| SUB1868 | | | |
| serine proteinase | SUB_NSP_FN | NdeI | CGCGCGCATATGACAAATCTTAATAAC |
| YP_002563137 | SUB_NSP_RX | XhoI | CGCGCGCTCGAGTTATTTTTCTAAATCTTTGGT |

*Target genes are listed according to their locus tag within the S. uberis 0140J genome (accession number NC 012004), and the name and accession number of the products they encode.

Preliminary appraisal of the expression of each of the 14 proteins was conducted). Following electrophoresis through polyacrylamide gels, recombinant products were excised and subjected to MALDI-ToF MS. Mass spectrometric data was searched against the fully-annotated S. uberis 0140J genome sequence (NC 012004) using the MASCOT search algorithm to confirm the identities of the recombinant proteins (data not shown). Subsequently, 4 were chosen (based on the level of expression) for assessment in a preliminary vaccination experiment.

Up-Scaled Expression of Candidate Antigens

The 4 antigens chosen for further study were (N.B. 'r' prefix denotes recombinant product) rSUB423 (ferrichrome binding protein), rSUB604 (elongation factor Tu), rSUB950 (lipoprotein) and rSUB1868 (serine protease). The coding sequences of each of the 4 antigens, and the corresponding translated amino acid sequences are presented in Table 3 (above).

Starter cultures of Escherichia coli BL21(DE3) containing each of the 4 recombinant plasmids were propagated in Lysogenic Broth (LB) containing 50 μg/ml of carbenicillin, overnight at 37° C. with shaking. These were then used to inoculate 1 l volumes of LB (containing 50 μg/ml of carbenicillin) in 5 l conical flasks. Cultures were shaken at 37° C. until an $OD_{600nm}$ of 0.6 was reached. Expression of the recombinant genes was induced by supplementation of cultures with IPTG to a final concentration of 1 mM; incubation was then continued as before for a further 1 h, then rifampicin was added to a final concentration of 150 μg/ml and incubation was continued for a further 3 h. Cells were harvested by centrifugation at 12,000×g for 15 m at 4° C., and cell pellets containing recombinant proteins were retained. Two of the recombinant proteins (rSUB950 and rSUB1868) remained soluble during expression and could be purified under native conditions. In contrast, the remaining proteins (rSUB423 and rSUB604) formed inclusion bodies during extraction and required purification under denaturing conditions.

Protein Purification Under Native Conditions

The cell pellets containing rSUB950 and rSUB1868 were re-suspended in 20 ml each of lysis buffer (1× BugBuster protein extraction reagent (Merck Millipore), 50 mM Tris HCl pH 8.0, 500 mM NaCl, 10 mM imidazole, 25 U/ml Benzonase enzyme (Merck Millipore) and 1× Complete EDTA-free protease inhibitor cocktail (Roche Applied Science)) and incubated at 37° C. for 60 min to allow cell lysis and degradation of nucleic acids. Cell lysates were centrifuged at 22,000×g for 30 m at 4° C. to pellet cell debris. Then, recombinant proteins in the clarified supernatants were recovered by immobilized metal ion affinity chromatography (IMAC) using Ni-CAM resin (Sigma). For each protein, 2×12 ml Eco-Pac Chromatography Columns (Bio-Rad) were loaded with 2 ml (bed volume) resin and washed by gravity flow with 10 ml of Equilibration Buffer (50 mM Tris HCl pH 8.0, 500 mM NaCl, 10 mM imidazole, 1× Complete EDTA-free protease inhibitor cocktail). The outlet of each column was sealed, and for each clarified lysate, 10 ml was added to each of 2 columns prior to sealing the inlet of each column with Parafilm (VWR). Columns were incubated on a tube rotator, overnight at 4° C. After incubation, columns were drained by gravity flow, and washed with 8×5 ml of Wash Buffer (50 mM Tris HCl pH 8.0, 500 mM NaCl, 10 mM imidazole, 1× Complete EDTA-free protease inhibitor cocktail). The recombinant protein in each column, bound to the Ni-CAM resin via the N-terminal 6×his tag, was eluted in 5×2 ml of Elution Buffer (50 mM Tris HCl pH 8.0, 500 mM NaCl, 250 mM imidazole, 1× Complete EDTA-free protease inhibitor cocktail). Subsequently, the eluate of equivalent proteins was pooled, and each protein was concentrated using Amicon Ultra-15, 10 kDa $M_r$ cut-off, centrifugal filter units, as per the manufacturer's instructions.

Purification Under Denaturing Conditions

Cell pellets containing inclusion bodies were initially treated according to the native extraction protocol. Subsequently, cell pellets containing inclusion bodies were suspended in 20 ml of native lysis buffer. Lysozyme was added to a final concentration of 1 kU/ml and digestion was carried out at room temperature for 15 min. After incubation, an equal volume of BugBuster reagent (diluted in distilled water) was added to the suspensions, which were mixed by vortexing for 1 min and centrifuged at 5,000×g for 15 min at 4° C. to collect inclusion bodies. Inclusion body pellets were then washed a further 3 times with 1:10 diluted BugBuster, as previously. Finally, each inclusion body was dissolved in 20 ml of 8 M urea (pH 8.0) at room temperature for 15 m, and then centrifuged at 5,000×g for 15 m at room temperature to pellet (remove) insoluble material. Subsequently, purification of each protein was performed using Ni-CAM resin, as described elsewhere except that the column buffers used for native purification were replaced with: Equilibration Buffer (0.1 M sodium phosphate, 8 M urea pH 8.0), Wash Buffer (0.1 M sodium phosphate, 8 M urea pH 6.3), and Elution Buffer (0.1 M sodium phosphate, 8 M urea pH 4.5).

Size Exclusion High-Performance Liquid Chromatography (HPLC)

Size exclusion HPLC was performed using a Superose 12 10/300GL column (GE Healthcare) pre-equilibrated with 1×PBS, pH6.8 (for native, soluble proteins) or 8 M urea in 1×PBS, pH6.8 (for denatured, insoluble proteins). Individual injections of 200 ml were applied to the column and proteins were resolved over a period of 60 m at a flow rate of 0.5 ml/m. The proteins that eluted from the column were monitored spectrophotometrically at a wavelength of 280 nm. For each protein, fractions of 1 ml were collected, and those corresponding to peaks of UV-absorbent material were examined for the presence of protein by SDS-PAGE and Coomassie Brilliant Blue staining. For each protein, eluted fractions observed to contain an enriched source of the protein of interest were pooled and concentrated by centrifugation with amicon ultra filters (10 kDa cut off).

Each of the 4 recombinant proteins was subjected to MALD-TOF MS, and mass spectrometric data was searched against the fully-annotated *S. uberis* 0140J genome sequence (NC 012004) using the MASCOT search algorithm to confirm that the identities of the recombinant proteins were as expected (data not shown).

SUMMARY

In order to facilitate the development of a new mastitis vaccine, we have conducted a study to identify those proteins which are produced by a diverse sub-set of the *S. uberis* population. The work was conducted with no prior assumption that any particular class of protein (e.g. putative virulence factor) would signify a better vaccine candidate than any other class of protein, but rather that conservation between species was of primary importance.

Preliminary proteomic analysis of the cell-wall sub-cellular fraction of a number of diverse *S. uberis* strains allowed the identification of a panel of candidate antigens. Subsequently, the carriage of the genes encoding these antigens was assessed among a wider population of *S. uberis* strains. In so doing, the panel of candidate antigens was refined further, and proof of concept that these antigens could be used as vaccine(s) was obtained by production of recombinant derivatives of 4 of the proteins, and using these to successfully protect dairy cattle against mastitis following experimental heterologous challenge with *S. uberis* (see Example 2 below).

EXAMPLE 2

*S. uberis* Vaccines in Cattle

*Streptococcus uberis* is Gram-positive bacterium, with a cell wall structure similar to *Staphylococcus* spp., as well as other streptococci such as *S. agalactiae* and *S. dysgalactiae*. *Streptococcus uberis* is the most common *Streptococcus* species isolated from cases of mastitis. The *S. uberis* is found in the udder, in the intestine, and on the cow's skin and teats, which is where most streptococci tend to be. The particularity of *S. uberis* is its extraordinary ability to contaminate the external environment, i.e. in the bedding or anywhere on an animal. The contamination can take place during milking or from subsequent contact with *S. uberis* elsewhere in the environment. The particular ecology of *S. uberis* makes it particularly difficult to fight against this bacterium.

Materials, Methods and Results

Antigens

The potential antigens, described above, were used for vaccination of cows against *S. uberis*. Specifically, the following antigens were selected for the study:

SUB0423-ferrichrome binding protein
SUB0604—elongation factor Tu
SUB0950—lipoprotein
SUB1868—Serine protease The treatments were as follows:

TABLE 13

| Group | Antigen | Concentration | Adjuvant |
|---|---|---|---|
| T01 | Saline | N/A | Saline: 0.85% NaCl |
| T02 | SUB0423 + SUB0604 | 75 ug/2 ml | TXO: CpG 250 ug |
| T03 | SUB0950 + SUB1868 | | (SEQID NO: 8)/ |
| | | | Dextran DEAE |
| T04 | 0423 + 0604 + 0950 + 1868 | | 100 mg/Oil 51% v/v |

Animals were allotted at day −7 and vaccinated on days zero and 28. Calving occurred on ~day 49. Samples of blood and milk were taken on days zero, 7, 28, 35, 49, 63, 70, and 84. The cows were challenged on day 70.

All calves were born alive in groups T2 and T4. One calf (out of 10) in T01 was still born. One calf (out of 10) in T03 died due to dystocia.

The following milk quality scoring system was implemented to indicate severity of abnormal signs:
0=Normal
1=Flakes
2=Slugs/Clots
3=Stringy/Watery/Bloody The results of milk evaluation are summarized in Table 8 below:

TABLE 14

| | Milk Appearance: At least 1 quarter with score equal or greater than 2? | | | | |
|---|---|---|---|---|---|
| | No | | Yes | | Total |
| | Number | % | Number | % | Number |
| T01 | 1 | 14.3 | 6 | 85.7 | 7 |
| T02 | 2 | 25 | 6 | 75 | 8 |
| T03 | 1 | 11.1 | 8 | 88.9 | 9 |
| T04 | 4 | 50 | 4 | 50 | 8 |

The following udder evaluation scoring system was implemented:
0=Normal
1=Slight swelling
2=Moderate swelling
3=Severe The results of udder evaluation are summarized in Table 9 below:

TABLE 15

Udder Evaluation:
At least 1 quarter with
score equal or greater than 2?

|  | No | | Yes | | Total |
| --- | --- | --- | --- | --- | --- |
|  | Number | % | Number | % | Number |
| T01 | 1 | 14.3 | 6 | 85.7 | 7 |
| T02 | 2 | 25 | 6 | 75 | 8 |
| T03 | 1 | 11.1 | 8 | 88.9 | 9 |
| T04 | 4 | 50 | 4 | 50 | 8 |

These results demonstrate that a combination antigen (as in T04) provides the best protection against mastitis, without affecting the calving of treated cows.

REFERENCES

1) HARDIE, J. M. 1986 Other streptococci. In *Bergey's Manual of Systematic Bacteriology* Vol. 2, ed. Sneath, P. H. A., Mair, N. S., Sharp, M. E. & Holt, J. G. pp. 1068-1071. Baltimore: Williams & Wilkins.
2) T. J. Coffey, G. D. Pullinger, R. Urwin, K. A. Jolley, S. M. Wilson, M. C. Maiden, J. A. Leigh First insights into the evolution of *Streptococcus uberis*: A multilocus sequence typing scheme that enables investigation of its population biology. Appl. Environ. Microbiol., 72 (2006), pp. 1420-1428
3) Williams A M, Collins M D. 1990. Molecular taxonomic studies on *Streptococcus uberis* types I and II. Description of *Streptococcus parauberis* sp. nov. J. Appl. Bacteriol. 68:485-490.
4) Nho S W, Hikima J, Cha I S, Park S B, Jang H B, del Castillo C S, Kondo H, Hirono I, Aoki T, Jung T S. 2011. Complete genome sequence and immunoproteomic analyses of the bacterial fish pathogen *Streptococcus parauberis*. Journal of Bacteriology. 193:3356-3366.
5) Altschul, S. F., Gish, W., Miller, W., Myers, E. W. & Lipman, D. J. (1990) "Basic local alignment search tool." J. Mol. Biol. 215:403-410.

The invention claimed is:

1. A method of raising a protective anti-*Streptococcus uberis* immune response in an animal, said method comprising the step of administering to the animal, an amount of a *Streptococcus uberis* antigen having the amino acid sequence of SEQ ID NO: 4 and a *Streptococcus uberis* antigen having the amino acid sequence of SEQ ID NO: 2 sufficient to induce the protective anti-*Streptococcus uberis* immune response.

2. The method of claim 1, wherein the *Streptococcus uberis* antigens are administered to the animal together with an adjuvant.

3. The method of claim 1, wherein the immune response is a response which is protective against the development of diseases caused or contributed to by *S. uberis* and/or against mastitis.

4. The method of claim 1, wherein the animal is a human, porcine, bovine, piscine, caprine and/or ovine animal.

* * * * *

SEQUENCE LISTING

<160> NUMBER OF SEQ ID NOS: 24

<210> SEQ ID NO 1
<211> LENGTH: 944
<212> TYPE: DNA
<213> ORGANISM: Artificial
<220> FEATURE:
<223> OTHER INFORMATION: rSUB0423 ferrichrome binding protein coding sequence

<400> SEQUENCE: 1

```
atgggcagca gccatcatca tcatcatcac agcagcggcc tggtgccgcg cggcagccat      60
atgctcgaga tgtcacaaag cacaaagcaa gaagatcata aaacaaaact atcacaaatg     120
ccaaagatct ctggttttac ctataaaggg aaggtaccag aaaaccctaa aagagtagtt     180
agtttatctt caacctacac cggttatttg gcaaagctcg atatcccact agttggaatc     240
acttcttatg atcacaaaaa tcccgtctta aagaaataca tcaaggatgc taaagttgtc     300
tctgcaaccg acctagaaag cattacggcc ttggaacctg atttaattat tgtgggttca     360
aatgaagaaa atatcagtca attagctgaa atcgctcccc ttatttccat tgaataccgc     420
aaacatgact atttacaggt attctcagat tttggtaaag tctttaacaa aaccaaagaa     480
accgacaaat ggttacagga atggaaaaca aaaacagctt cttttgaaag tgacgttaaa     540
gcagttacag gtaataatgc taccttttacc ataatgggat tatatgagaa agatatctat     600
cttttcggta aagattgggg tcgtggtggt gaaatcattc accaagcctt ccaatatcaa     660
gctccagaaa aagtaaaaat ggaggttttc ccaaaaggct atttgtccat ttcacaagaa     720
gttcttccag attatattgg tgattatgtc gttgtcgctg cagaggatga aaaaacaggt     780
tcttctcttt atgaaagtga cctttggaaa aatataccag ccgttcaaaa aaatcatgtc     840
ataaatgtta atgcgaatac cttttatttc actgaccctc tgtcattaga gtatgaatta     900
aaaaccttaa cggatgctat cttgactcag aaaactcaca acta                      944
```

<210> SEQ ID NO 2

<211> LENGTH: 314
<212> TYPE: PRT
<213> ORGANISM: Artificial
<220> FEATURE:
<223> OTHER INFORMATION: rSUB0423 ferrichrome binding protein

<400> SEQUENCE: 2

| | | | | | | | | | | | | | | | |
|---|---|---|---|---|---|---|---|---|---|---|---|---|---|---|---|
| Met | Gly | Ser | Ser | His | His | His | His | His | Ser | Ser | Gly | Leu | Val | Pro | |
| 1 | | | | 5 | | | | | 10 | | | | | 15 | |
| Arg | Gly | Ser | His | Met | Leu | Glu | Met | Ser | Gln | Ser | Thr | Lys | Gln | Glu | Asp |
| | | | 20 | | | | | 25 | | | | | 30 | | |
| His | Lys | Thr | Lys | Leu | Ser | Gln | Met | Pro | Lys | Ile | Ser | Gly | Phe | Thr | Tyr |
| | | | 35 | | | | | 40 | | | | | 45 | | |
| Lys | Gly | Lys | Val | Pro | Glu | Asn | Pro | Lys | Arg | Val | Val | Ser | Leu | Ser | Ser |
| 50 | | | | | 55 | | | | | 60 | | | | | |
| Thr | Tyr | Thr | Gly | Tyr | Leu | Ala | Lys | Leu | Asp | Ile | Pro | Leu | Val | Gly | Ile |
| 65 | | | | 70 | | | | | 75 | | | | | 80 | |
| Thr | Ser | Tyr | Asp | His | Lys | Asn | Pro | Val | Leu | Lys | Lys | Tyr | Ile | Lys | Asp |
| | | | | 85 | | | | | 90 | | | | | 95 | |
| Ala | Lys | Val | Val | Ser | Ala | Thr | Asp | Leu | Glu | Ser | Ile | Thr | Ala | Leu | Glu |
| | | | 100 | | | | | 105 | | | | | 110 | | |
| Pro | Asp | Leu | Ile | Ile | Val | Gly | Ser | Asn | Glu | Glu | Asn | Ile | Ser | Gln | Leu |
| | | | 115 | | | | | 120 | | | | | 125 | | |
| Ala | Glu | Ile | Ala | Pro | Leu | Ile | Ser | Ile | Glu | Tyr | Arg | Lys | His | Asp | Tyr |
| | | | 130 | | | | | 135 | | | | | 140 | | |
| Leu | Gln | Val | Phe | Ser | Asp | Phe | Gly | Lys | Val | Phe | Asn | Lys | Thr | Lys | Glu |
| 145 | | | | | 150 | | | | | 155 | | | | | 160 |
| Thr | Asp | Lys | Trp | Leu | Gln | Glu | Trp | Lys | Thr | Lys | Thr | Ala | Ser | Phe | Glu |
| | | | | 165 | | | | | 170 | | | | | 175 | |
| Ser | Asp | Val | Lys | Ala | Val | Thr | Gly | Asn | Asn | Ala | Thr | Phe | Thr | Ile | Met |
| | | | 180 | | | | | 185 | | | | | 190 | | |
| Gly | Leu | Tyr | Glu | Lys | Asp | Ile | Tyr | Leu | Phe | Gly | Lys | Asp | Trp | Gly | Arg |
| | | | 195 | | | | | 200 | | | | | 205 | | |
| Gly | Gly | Glu | Ile | Ile | His | Gln | Ala | Phe | Gln | Tyr | Gln | Ala | Pro | Glu | Lys |
| | | | 210 | | | | | 215 | | | | | 220 | | |
| Val | Lys | Met | Glu | Val | Phe | Pro | Lys | Gly | Tyr | Leu | Ser | Ile | Ser | Gln | Glu |
| 225 | | | | | 230 | | | | | 235 | | | | | 240 |
| Val | Leu | Pro | Asp | Tyr | Ile | Gly | Asp | Tyr | Val | Val | Ala | Ala | Glu | Asp | |
| | | | | 245 | | | | | 250 | | | | | 255 | |
| Glu | Lys | Thr | Gly | Ser | Ser | Leu | Tyr | Glu | Ser | Asp | Leu | Trp | Lys | Asn | Ile |
| | | | 260 | | | | | 265 | | | | | 270 | | |
| Pro | Ala | Val | Gln | Lys | Asn | His | Val | Ile | Asn | Val | Asn | Ala | Asn | Thr | Phe |
| | | | 275 | | | | | 280 | | | | | 285 | | |
| Tyr | Phe | Thr | Asp | Pro | Leu | Ser | Leu | Glu | Tyr | Glu | Leu | Lys | Thr | Leu | Thr |
| | | | 290 | | | | | 295 | | | | | 300 | | |
| Asp | Ala | Ile | Leu | Thr | Gln | Lys | Thr | His | Asn | | | | | | |
| 305 | | | | | 310 | | | | | | | | | | |

<210> SEQ ID NO 3
<211> LENGTH: 1265
<212> TYPE: DNA
<213> ORGANISM: Artificial
<220> FEATURE:
<223> OTHER INFORMATION: rSUB0604 elongation factor Tu coding sequence

<400> SEQUENCE: 3
tgggcagcag ccatcatcat catcatcaca gcagcggcct ggtgccgcgc ggcagccata    60

```
tgctcgagat ggcaaaagaa aaatacgatc gtagtaaacc ccacgttaac attggtacaa      120
ttggacacgt tgaccacggt aaaactactt tgacagctgc aattacaact gtacttgctc      180
gtcgcttacc aacttcagtt aaccaaccaa aagattacgc ttctatcgat gctgctccag      240
aagagcgcga acgcggaatc actatcaaca ctgcacacgt tgagtacgaa actgaaactc      300
gtcactatgc ccacattgat gccccaggac acgcggacta tgttaaaaac atgatcactg      360
gtgctgccca atggacgga gctatccttg ttgttgcatc aactgatgga ccaatgccac       420
aaactcgtga gcacatcctt ctttcacgcc aagttggtgt taaacacctt atcgttttca      480
tgaacaaaat cgaccttgtt gacgatgaag aattgcttga attagttgaa atggaaatcc      540
gtgaccttct ttcagaatac gatttcccag gtgatgacct accagttatc caaggttcag      600
ctcttaaagc tcttgaaggt gattctaaat acgaagacat catcatggaa ttgatgaaaa      660
ctgctgatga gtatattcca gaaccagaac gtgatacaga caaaccatta cttcttccag      720
tcgaagacgt attctcaatc acaggtcgtg gtactgtagc ttcaggacgt atcgatcgtg      780
gtactgttcg tgtcaacgac gaaattgaaa tcgttggtat caagaagaa actaaaaaag      840 cagttgttac tggtgttgaa atgttccgta acaacttga cgaaggtctt gcaggagata       900
acgtaggtat ccttcttcgt ggtgttcaac gtgacgaaat cgaacgtgga caagttattg      960
ctaaaccagg ttcaatcaac ccacacacta aattcaaagg tgaagtttac atcctttcta     1020
aagatgaagg tggacgtcat actccattct tcaacaacta ccgtcctcaa ttctatttcc     1080
gtacaactga cgtaacaggt tcaatcgaac ttccagctgg tactgaaatg gtaatgcctg     1140
gtgataacgt gacaatcagc gttgagttga tccacccaat cgccgttgaa caaggtacta     1200
ctttctcaat ccgtgaaggt ggacgtactg ttggttcagg tattgtttca gaaatcgaag     1260
cttaa                                                                  1265
```

<210> SEQ ID NO 4
<211> LENGTH: 421
<212> TYPE: PRT
<213> ORGANISM: Artificial
<220> FEATURE:
<223> OTHER INFORMATION: rSUB0604 elongation factor Tu

<400> SEQUENCE: 4

```
Met Gly Ser Ser His His His His His His Ser Ser Gly Leu Val Pro
1               5                   10                  15

Arg Gly Ser His Met Leu Glu Met Ala Lys Glu Lys Tyr Asp Arg Ser
            20                  25                  30

Lys Pro His Val Asn Ile Gly Thr Ile Gly His Val Asp His Gly Lys
        35                  40                  45

Thr Thr Leu Thr Ala Ala Ile Thr Thr Val Leu Ala Arg Arg Leu Pro
    50                  55                  60

Thr Ser Val Asn Gln Pro Lys Asp Tyr Ala Ser Ile Asp Ala Ala Pro
65                  70                  75                  80

Glu Glu Arg Glu Arg Gly Ile Thr Ile Asn Thr Ala His Val Glu Tyr
                85                  90                  95

Glu Thr Glu Thr Arg His Tyr Ala His Ile Asp Ala Pro Gly His Ala
            100                 105                 110

Asp Tyr Val Lys Asn Met Ile Thr Gly Ala Ala Gln Met Asp Gly Ala
        115                 120                 125

Ile Leu Val Val Ala Ser Thr Asp Gly Pro Met Pro Gln Thr Arg Glu
    130                 135                 140
```

His Ile Leu Leu Ser Arg Gln Val Gly Val Lys His Leu Ile Val Phe
145                 150                 155                 160

Met Asn Lys Ile Asp Leu Val Asp Asp Glu Leu Leu Glu Leu Val
            165                 170                 175

Glu Met Glu Ile Arg Asp Leu Leu Ser Glu Tyr Asp Phe Pro Gly Asp
            180                 185                 190

Asp Leu Pro Val Ile Gln Gly Ser Ala Leu Lys Ala Leu Glu Gly Asp
            195                 200                 205

Ser Lys Tyr Glu Asp Ile Ile Met Glu Leu Met Lys Thr Ala Asp Glu
            210                 215                 220

Tyr Ile Pro Glu Pro Glu Arg Asp Thr Asp Lys Pro Leu Leu Leu Pro
225                 230                 235                 240

Val Glu Asp Val Phe Ser Ile Thr Gly Arg Gly Thr Val Ala Ser Gly
                245                 250                 255

Arg Ile Asp Arg Gly Thr Val Arg Val Asn Asp Glu Ile Glu Ile Val
            260                 265                 270

Gly Ile Lys Glu Glu Thr Lys Lys Ala Val Val Thr Gly Val Glu Met
            275                 280                 285

Phe Arg Lys Gln Leu Asp Glu Gly Leu Ala Gly Asp Asn Val Gly Ile
290                 295                 300

Leu Leu Arg Gly Val Gln Arg Asp Glu Ile Glu Arg Gly Gln Val Ile
305                 310                 315                 320

Ala Lys Pro Gly Ser Ile Asn Pro His Thr Lys Phe Lys Gly Glu Val
                325                 330                 335

Tyr Ile Leu Ser Lys Asp Glu Gly Gly Arg His Thr Pro Phe Phe Asn
            340                 345                 350

Asn Tyr Arg Pro Gln Phe Tyr Phe Arg Thr Thr Asp Val Thr Gly Ser
            355                 360                 365

Ile Glu Leu Pro Ala Gly Thr Glu Met Val Met Pro Gly Asp Asn Val
370                 375                 380

Thr Ile Ser Val Glu Leu Ile His Pro Ile Ala Val Glu Gln Gly Thr
385                 390                 395                 400

Thr Phe Ser Ile Arg Glu Gly Gly Arg Thr Val Gly Ser Gly Ile Val
                405                 410                 415

Ser Glu Ile Glu Ala
            420

<210> SEQ ID NO 5
<211> LENGTH: 1041
<212> TYPE: DNA
<213> ORGANISM: Artificial
<220> FEATURE:
<223> OTHER INFORMATION: rSUB0950 lipoprotein coding sequence

<400> SEQUENCE: 5
atgggcagca gccatcatca tcatcatcac agcagcggcc tggtgccgcg cggcagccat      60
atgctcgaga tggatagcaa agatgctaaa acagatttaa aagctgctat tgttactgat     120
acaggtggtg ttgatgataa atcatttaac caatctgctt gggaaggttt agaagcttgg     180
ggtaaagaaa atgggcttaa aaaaggtgct ggtttcgact acttccaatc aaatagtgaa     240
tcagaatatg ctactaatct tgacactgct gtctcaagtg ttataacgt agtatatgga      300 atcggatttg cccttaaaga tgcaattgat aaagctgctg gtgacaatag tgatgttaac     360
tatattatcg ttgacgatgt catcgaagga aaagataatg ttgcaagtgt aacttttgcg     420

-continued

```
gataacgaag ctgcttatct tgctggtatt gctgcagcta aaactacaaa aactaaagta      480
gtaggttttg taggtggtat ggaaggtact gttatcactc gttttgaaaa aggttttgag      540
gcgggagtga atcagttga tgattctatc caaatcaaag ttgactacgc tggatcattt       600
ggtgatgctg ctaaaggtaa aacaattgcc gcagctcaat atgcaggtgg tgctgacgtt      660
atttatcaag ccgctggtgg tactggagca ggtgtcttca atgaagctaa agctgtaaat      720
gagaaaaaag atgaagctga taagttttgg gtaatcggtg tagaccgtga ccaaaaagag      780
gaaggtaaat acacttcaaa agacggtaaa gaatctaact ttgttctagc atcttcaatt      840
aaacaagttg gtaaatctgt acaactgatt aacaaacttg ttactgataa aaaattccct      900
ggtggaaaaa caactgttta tggattaaaa gatggtggtg ttgatattgc aacaacaaac      960
ctttctgatg atgctataaa agctgttaaa gaagctaaag aaaaaattat ttctggcgat    1020
gtaaaagttc ctgaaaaata a                                               1041
```

<210> SEQ ID NO 6
<211> LENGTH: 346
<212> TYPE: PRT
<213> ORGANISM: Artificial
<220> FEATURE:
<223> OTHER INFORMATION: rSUB0950 lipoprotein

<400> SEQUENCE: 6

```
Met Gly Ser Ser His His His His His His Ser Ser Gly Leu Val Pro
 1               5                  10                  15

Arg Gly Ser His Met Leu Glu Met Asp Ser Lys Asp Ala Lys Thr Asp
            20                  25                  30

Leu Lys Ala Ala Ile Val Thr Asp Thr Gly Gly Val Asp Asp Lys Ser
        35                  40                  45

Phe Asn Gln Ser Ala Trp Glu Gly Leu Glu Ala Trp Gly Lys Glu Asn
    50                  55                  60

Gly Leu Lys Lys Gly Ala Gly Phe Asp Tyr Phe Gln Ser Asn Ser Glu
65                  70                  75                  80

Ser Glu Tyr Ala Thr Asn Leu Asp Thr Ala Val Ser Ser Gly Tyr Asn
                85                  90                  95

Val Val Tyr Gly Ile Gly Phe Ala Leu Lys Asp Ala Ile Asp Lys Ala
            100                 105                 110

Ala Gly Asp Asn Ser Asp Val Asn Tyr Ile Ile Val Asp Val Ile
        115                 120                 125

Glu Gly Lys Asp Asn Val Ala Ser Val Thr Phe Ala Asp Asn Glu Ala
    130                 135                 140

Ala Tyr Leu Ala Gly Ile Ala Ala Lys Thr Thr Lys Thr Lys Val
145                 150                 155                 160

Val Gly Phe Val Gly Gly Met Glu Gly Thr Val Ile Thr Arg Phe Glu
                165                 170                 175

Lys Gly Phe Glu Ala Gly Val Lys Ser Val Asp Asp Ser Ile Gln Ile
            180                 185                 190

Lys Val Asp Tyr Ala Gly Ser Phe Gly Asp Ala Ala Lys Gly Lys Thr
        195                 200                 205

Ile Ala Ala Ala Gln Tyr Ala Gly Gly Ala Asp Val Ile Tyr Gln Ala
    210                 215                 220

Ala Gly Gly Thr Gly Ala Gly Val Phe Asn Glu Ala Lys Ala Val Asn
225                 230                 235                 240

Glu Lys Lys Asp Glu Ala Asp Lys Val Trp Val Ile Gly Val Asp Arg
                245                 250                 255
```

Asp Gln Lys Glu Glu Gly Lys Tyr Thr Ser Lys Asp Gly Lys Glu Ser
            260                 265                 270

Asn Phe Val Leu Ala Ser Ser Ile Lys Gln Val Gly Lys Ser Val Gln
        275                 280                 285

Leu Ile Asn Lys Leu Val Thr Asp Lys Lys Phe Pro Gly Gly Lys Thr
    290                 295                 300

Thr Val Tyr Gly Leu Lys Asp Gly Val Asp Ile Ala Thr Thr Asn
305                 310                 315                 320

Leu Ser Asp Asp Ala Ile Lys Ala Val Lys Glu Ala Lys Glu Lys Ile
                325                 330                 335

Ile Ser Gly Asp Val Lys Val Pro Glu Lys
            340                 345

<210> SEQ ID NO 7
<211> LENGTH: 1149
<212> TYPE: DNA
<213> ORGANISM: Artificial
<220> FEATURE:
<223> OTHER INFORMATION: rSUB1868 serine proteinase coding sequence

<400> SEQUENCE: 7

```
atgggcagca gccatcatca tcatcatcac agcagcggcc tggtgccgcg cggcagccat      60
atgacaaatc ttaataaccc aacgacgaca agtaaagtaa cctataaaaa tactactaat     120
acgactaaag ctgttaaagt gattcaagat gcagttgttt ctgtagttaa ctatcaaaaa     180
aatgattctt taaactcagc catggatatt tttagtcaag gtgattcatc aactaaagag     240
aatgatggac tttctattta gtgaagga tcaggtgtta tatacaaaaa agatggtgat      300
tctgcatatc tggtaaccaa caaccacgta atagacaaag ctgaaagaat tgaaattatt     360
ttagctgatg gttcaaaagt tgttgggaaa ttaattggtg ctgacactta ttctgacctg     420
gctgttgtaa aaatttcttc agacaaaatt aagactgtag ctcagtttgc agattcttcc     480
aaaataaaca taggtgaagt tgcaattgca attggtagtc ctcttggaac agaatatgct     540
aattccgtaa ctgaaggaat tgtttcaagt ttaagtagaa cagtaacttt aaaaaatgaa     600
gaaggacaaa ctgtttcaac taatgccatt caaacagatg ctgctattaa ccctggaaac     660
tctggcggac ctttaattaa tattgaagga caaattattg aataaactc tagcaaaatc     720
tcacagtcta atcatctggg aaatgcagtc gaaggaatgg gatttgcaat tccagctaat     780
gacgttatta aaattattaa ccaacttgaa agcaaaggcg aagtagttcg acctgcatta     840
ggtatttcaa tggttaatct aagtgattta tcaacaaatg cccttgatca gctcaaagtt     900
ccaaaaaatg ttactagtgg tatcgtagtt gctaaagtcg tagacaatat gcctgcctca     960
ggaaaacttg aacaatatga tattatcact gaaattgatg gggaagaagt gagcagtaca    1020
agtgatttac aaagtattct gtatgggcat gatattaatg ataccgtaaa agtcacttt     1080
tatagaggta tgataagaa atctactact attgaattaa ctaaaactac caagatttta    1140
gaaaaataa                                                             1149
```

<210> SEQ ID NO 8
<211> LENGTH: 382
<212> TYPE: PRT
<213> ORGANISM: Artificial
<220> FEATURE:
<223> OTHER INFORMATION: rSUB1868 serine proteinase

<400> SEQUENCE: 8

```
Met Gly Ser Ser His His His His His Ser Ser Gly Leu Val Pro
1               5                   10                  15

Arg Gly Ser His Met Thr Asn Leu Asn Pro Thr Thr Ser Lys
            20              25              30

Val Thr Tyr Lys Asn Thr Thr Asn Thr Lys Ala Val Lys Val Ile
        35              40              45

Gln Asp Ala Val Val Ser Val Asn Tyr Gln Lys Asn Asp Ser Leu
50              55              60

Asn Ser Ala Met Asp Ile Phe Ser Gln Gly Ser Ser Thr Lys Glu
65              70              75              80

Asn Asp Gly Leu Ser Ile Tyr Ser Glu Gly Ser Gly Val Ile Tyr Lys
                85              90              95

Lys Asp Gly Asp Ser Ala Tyr Leu Val Thr Asn Asn His Val Ile Asp
            100             105             110

Lys Ala Glu Arg Ile Glu Ile Ile Leu Ala Asp Gly Ser Lys Val Val
            115             120             125

Gly Lys Leu Ile Gly Ala Asp Thr Tyr Ser Asp Leu Ala Val Val Lys
    130             135             140

Ile Ser Ser Asp Lys Ile Lys Thr Val Ala Gln Phe Ala Asp Ser Ser
145             150             155             160

Lys Ile Asn Ile Gly Glu Val Ala Ile Ala Ile Gly Ser Pro Leu Gly
            165             170             175

Thr Glu Tyr Ala Asn Ser Val Thr Glu Gly Ile Val Ser Ser Leu Ser
            180             185             190

Arg Thr Val Thr Leu Lys Asn Glu Gly Gln Thr Val Ser Thr Asn
    195             200             205

Ala Ile Gln Thr Asp Ala Ala Ile Asn Pro Gly Asn Ser Gly Gly Pro
    210             215             220

Leu Ile Asn Ile Glu Gly Gln Ile Gly Ile Asn Ser Ser Lys Ile
225             230             235             240

Ser Gln Ser Lys Ser Gly Asn Ala Val Glu Gly Met Gly Phe Ala
            245             250             255

Ile Pro Ala Asn Asp Val Ile Lys Ile Asn Gln Leu Glu Ser Lys
            260             265             270

Gly Glu Val Val Arg Pro Ala Leu Gly Ile Ser Met Val Asn Leu Ser
    275             280             285

Asp Leu Ser Thr Asn Ala Leu Asp Gln Leu Lys Val Pro Lys Asn Val
    290             295             300

Thr Ser Gly Ile Val Val Ala Lys Val Val Asp Asn Met Pro Ala Ser
305             310             315             320

Gly Lys Leu Glu Gln Tyr Asp Ile Ile Thr Glu Ile Asp Gly Glu Glu
            325             330             335

Val Ser Ser Thr Ser Asp Leu Gln Ser Ile Leu Tyr Gly His Asp Ile
            340             345             350

Asn Asp Thr Val Lys Val Thr Phe Tyr Arg Gly Asn Asp Lys Lys Ser
            355             360             365

Thr Thr Ile Glu Leu Thr Lys Thr Thr Lys Asp Leu Glu Lys
    370             375             380

<210> SEQ ID NO 9
<211> LENGTH: 21
<212> TYPE: DNA
<213> ORGANISM: Artificial
<220> FEATURE:
<223> OTHER INFORMATION: PCR primer sequence
```

<400> SEQUENCE: 9
gttctaggag attagaattc a                                              21

<210> SEQ ID NO 10
<211> LENGTH: 21
<212> TYPE: DNA
<213> ORGANISM: Artificial
<220> FEATURE:
<223> OTHER INFORMATION: PCR primer sequence

<400> SEQUENCE: 10
tttggtttgt gtccgtcata a                                              21

<210> SEQ ID NO 11
<211> LENGTH: 25
<212> TYPE: DNA
<213> ORGANISM: Artificial
<220> FEATURE:
<223> OTHER INFORMATION: PCR primer sequence

<400> SEQUENCE: 11
agtaaggtaa agttagactg tattg                                          25

<210> SEQ ID NO 12
<211> LENGTH: 25
<212> TYPE: DNA
<213> ORGANISM: Artificial
<220> FEATURE:
<223> OTHER INFORMATION: PCR primer sequence

<400> SEQUENCE: 12
agttgtctga ctctaattgt taatc                                          25

<210> SEQ ID NO 13
<211> LENGTH: 19
<212> TYPE: DNA
<213> ORGANISM: Artificial
<220> FEATURE:
<223> OTHER INFORMATION: PCR primer sequence

<400> SEQUENCE: 13
gttattggcc ataaggcta                                                 19

<210> SEQ ID NO 14
<211> LENGTH: 18
<212> TYPE: DNA
<213> ORGANISM: Artificial
<220> FEATURE:
<223> OTHER INFORMATION: PCR primer sequence

<400> SEQUENCE: 14
taaggtcgct ccacattt                                                  18

<210> SEQ ID NO 15
<211> LENGTH: 17
<212> TYPE: DNA
<213> ORGANISM: Artificial
<220> FEATURE:
<223> OTHER INFORMATION: PCR primer sequence

<400> SEQUENCE: 15
aggtaatgcc gtgtcta                                                   17

<210> SEQ ID NO 16

```
<211> LENGTH: 18
<212> TYPE: DNA
<213> ORGANISM: Artificial
<220> FEATURE:
<223> OTHER INFORMATION: PCR primer sequence

<400> SEQUENCE: 16
atgaatccga ggttggta                                              18

<210> SEQ ID NO 17
<211> LENGTH: 30
<212> TYPE: DNA
<213> ORGANISM: Artificial
<220> FEATURE:
<223> OTHER INFORMATION: PCR primer sequence

<400> SEQUENCE: 17
cgcgcgctcg agatgtcaca aagcacaaag                                 30

<210> SEQ ID NO 18
<211> LENGTH: 30
<212> TYPE: DNA
<213> ORGANISM: Artificial
<220> FEATURE:
<223> OTHER INFORMATION: PCR primer sequence

<400> SEQUENCE: 18
cgcgcgggat ccctagttgt gagttttctg                                 30

<210> SEQ ID NO 19
<211> LENGTH: 30
<212> TYPE: DNA
<213> ORGANISM: Artificial
<220> FEATURE:
<223> OTHER INFORMATION: PCR primer sequence

<400> SEQUENCE: 19
cgcgcgctcg agatggcaaa agaaaaatac                                 30

<210> SEQ ID NO 20
<211> LENGTH: 30
<212> TYPE: DNA
<213> ORGANISM: Artificial
<220> FEATURE:
<223> OTHER INFORMATION: PCR primer sequence

<400> SEQUENCE: 20
cgcgcgggat ccttaagctt cgatttctga                                 30

<210> SEQ ID NO 21
<211> LENGTH: 30
<212> TYPE: DNA
<213> ORGANISM: Artificial
<220> FEATURE:
<223> OTHER INFORMATION: PCR primer sequence

<400> SEQUENCE: 21
cgcgcgctcg agatggatag caaagatgct                                 30

<210> SEQ ID NO 22
<211> LENGTH: 33
<212> TYPE: DNA
<213> ORGANISM: Artificial
<220> FEATURE:
<223> OTHER INFORMATION: PCR primer sequence

<400> SEQUENCE: 22
```

-continued

```
cgcgcgggat ccttattatt tttcaggaac ttt                           33

<210> SEQ ID NO 23
<211> LENGTH: 27
<212> TYPE: DNA
<213> ORGANISM: Artificial
<220> FEATURE:
<223> OTHER INFORMATION: PCR primer sequence

<400> SEQUENCE: 23
cgcgcgcata tgacaaatct taataac                                  27

<210> SEQ ID NO 24
<211> LENGTH: 33
<212> TYPE: DNA
<213> ORGANISM: Artificial
<220> FEATURE:
<223> OTHER INFORMATION: PCR primer sequence

<400> SEQUENCE: 24
cgcgcgctcg agttattttt ctaaatcttt ggt                           33
```

UNITED STATES PATENT AND TRADEMARK OFFICE
CERTIFICATE OF CORRECTION

| | |
|---|---|
| PATENT NO. | : 10,744,192 B2 |
| APPLICATION NO. | : 15/074689 |
| DATED | : August 18, 2020 |
| INVENTOR(S) | : Fontaine et al. |

It is certified that error appears in the above-identified patent and that said Letters Patent is hereby corrected as shown below:

In the Specification

Column 28, Line 29: Please correct "TABLE 13" to read -- TABLE 7 --

Column 28, Line 55: Please correct "TABLE 14" to read -- TABLE 8 --

Column 29, Line 10: Please correct "TABLE 15" to read -- TABLE 9 --

Page 1 of 1

Signed and Sealed this
Ninth Day of March, 2021

Drew Hirshfeld
*Performing the Functions and Duties of the
Under Secretary of Commerce for Intellectual Property and
Director of the United States Patent and Trademark Office*